United States Patent [19]
Adams et al.

[11] Patent Number: 6,120,770
[45] Date of Patent: Sep. 19, 2000

[54] PLASMODIUM PROTEINS USEFUL FOR PREPARING VACCINE COMPOSITIONS

[75] Inventors: John H. Adams, Granger; Stefan Kappe, South Bend, both of Ind.; John P. Dalton, Dublin, Ireland

[73] Assignee: University of Notre Dame du Lac, Notre Dame, Ind.

[21] Appl. No.: 08/929,329

[22] Filed: Sep. 12, 1997

[51] Int. Cl.$^7$ ............... A61K 39/00; A61K 39/002; A61K 39/015; C07K 1/00

[52] U.S. Cl. .................... 424/185.1; 424/191.1; 424/268.1; 424/272.1; 530/300; 530/324; 530/325; 530/326; 530/327; 530/328; 530/329; 530/350

[58] Field of Search ............... 424/185.1, 191.1, 424/268.1, 272.1; 530/300, 350, 324, 325, 326, 327, 328, 329

[56] References Cited

FOREIGN PATENT DOCUMENTS

| | | |
|---|---|---|
| 187991 | 7/1986 | European Pat. Off. |
| 95/21192 | 8/1995 | WIPO . |

OTHER PUBLICATIONS

Glainski, M.R. and Barnwell, J.W., "*Plasmodium vivax*: merozites invasion of reticulocytes and considerations for malaria vaccine development", Parasitology Today, vol. 12, pp. 20–29, 1996.

Barnwell, J.W., Nichols, M.E. and Rubinstein, P., "In vitro evaluation of the role of the Duffy blood group in erythrocyte invasion by *Plasmodium vivax*", J. Exp. Med., No. 169, pp. 1795–17802, 1989.

Wertheimer, S.P., and Barnwell, J.W., "*Plasmodium vivax* interaction with the human Duffy blood group glycoprotein: identification of a parasite receptor–like protein", Exp. Parasitol, vol. 69, pp. 340–350, 1989.

Sim, B.K.L., Chitnis, C.E., Wasniowska, T.J., Hadley, T.J. and Miller L.H., "Receptor and ligand domains for invasion of erythrocytes by *Plasmodium falciparum*", Science, No. 264, 1941–1944, 1994.

Adams, J.H., Hudson, D.E., Torii, M., Ward, G.E., Wellems, T.E., Aikawa, M. and Miller, L.H., The Duffy receptor family of *Plasmodium knowlesi* is located within the micronemes of invasive malaria merozoties, Cell, vol. 63, pp. 141–153, 1990.

Adams, J.H., Sim, B.K.L., Dolan, S.A., Fang, X., Kaslow, D.C. and Miller, L.H., "A family of erythrocyte binding proteins of malaria parasites", Proc. Natl. Acad. Sci. USA, vol. 89, pp. 7085–7089, 1992.

Chitnis, C. and Miller, L.H., "Identification of the erythrocyte binding domains of *Plasmodium vivax* and *Plasmodium knowlesi* proteins involved in erythrocyte invasion", J. Exp. Med., vol. 180, pp. 497–506, 1994.

Peterson, D.C., Miller, L.H. and Wellems, T.E., "Isolation of multiple sequences from the *Plasmodium falciparum* genome that encode conserved domains homologous to those in erythrocyte binding proteins" Proc. Natl. Acad. Sci. USA, vol. 92, pp. 7100–7104,1995.

Aikawa, M., Miller, L.H., Johnson, J. and Rabbege, Jr., "Erythrocyte entry by malarial parasites. A moving junction between erythrocyte and parasite", J. Cell Biol., vol. 77, pp. 72–82, 1978.

Sim, B.K., Orlandi, P.A., Haynes, J.D., Klotz, F.W., Carter, J.M., Camus, D., Zegans, M.E. and Chulay, J.D., "Primary structure of 175K *Plasmodium falciparum* erythrocyte binding antigen and identification of a peptide which elicits antibodies that inhibit malaria merozoite invasion", J. Cell Biol., vol. 111, pp. 1877–1884, 1990.

*Primary Examiner*—Mark Navarro
*Attorney, Agent, or Firm*—Barnes & Thornburg; Alice O. Martin

[57] ABSTRACT

The present invention relates to DNA segments encoding MAEBL, an erythrocyte binding protein of a Plasmodium parasite, to substantially pure MAEBL proteins and to recombinantly or synthetically produced MAEBL molecules. The MAEBL proteins can be utilized as a vaccine for humans against malaria.

6 Claims, 3 Drawing Sheets

FIG. 1

```
YM - M1    -------------------NPQEDFMDRFDILNNHvnikwtnsgslaggnlkfdiydednis
Pb - M1    -------------------NPQEDFMDRFDILNNHvnikwtnsgslgkgdfkfdiydednin
Pf - M1
YM - M2    gtqdinlnrnnnynqpknkpNPQAEYMDRFDIEKNHiyidwkqdgkygsgklkyniiishetad
Pb - M2    gtqdinlkrnnnykqpknklNPQAEYMDRFDIEKNHiyidwkqdgkygsdklkyniiishetan
Pf - M2    ....................NNHifiewqkegeygndafkyniisnktag YM - M1    sklnslenar--lCpnnekgniYRGSCPDYGKTFSMD-----Ldkdeysedflneislgllnk
Pb - M1    skfntlesaq--lCsnhendgiYRGSCPDYGKTFSMN-----Ldkdeynedflneislgllnk
Pf - M1                    RGSCPDYGKTFLMG-----Fednkyseeflneisfgflnk
YM - M2    tiqsllitdkddiCpnhyspgrAGSCPNYGKSIVVKTPESINgnehlnsnflneirtgylnk
Pb - M2    tvqsllitdkndiCpnhyspgrAQGSCPNYGKSIIVKALEGTNgdeyfnlnflneirtgylnr
Pf - M2    tsqslfhnykdktCpnhvyegrAHGSCPNYGKAIIVQNLLGEEydknfnlnflneirtgylnk YM - M1    kllidveipvnmsglamyqglfanCpydknhvndiknеke--ydmCfdkfysnkqdistrikk
Pb - M1    kllidleipvnmsglamyqglfanCpydknhandikneke--ydmCfdkfyrnkqnistrikk
Pf - M1    kyklpieiplnksglsmyqglfkrCpynkkhysmiknene--ydmCfrkfynns-nistriyk
YM - M2    ymksnvelpyeksglamhhgdlsvCpkswdeenlykkardynydmCkstvmkstiplkmfdyk
Pb - M2    ymkydvelpyeksglamhhgdlneCpksldeenlykiksdynygmCkstvlksnvpfktynyr
Pf - M2    yfkkdveisyensgiamhnnmlrsCpvheneeklfsvktdynykmCkskifsnrftmkeydpk YM - M1    yplis-kytyfgshglggrlgsnteyplhiynpienyrtqkmRYPKLVETLEDCSIYShCigp
Pb - M1    qllis-kytyfgshglggrlgsnteyplhiynpienyktkqMRYPKLVETLEDCSIYShCigp
Pf - M1    rgkqnrkyiyfsshglggrlganieeplhkyykndehyvtk-mRYPeKNKKfvDCSIYShCigp
YM - M2    tk----kllyfglyglggrlgsniskvknifksqpnnitlpmfnpssiknlldCslysyClgp
Pb - M2    tk----kllyfglyglggrlgsnmskiknifksrpnnitlpmfnpsliknlldCslysyClgp
Pf - M2    tr----lfmyyglyglggrlganikrdqkakkyednitlpmknpsliknlfdCsiysyClgp YM - M1    CfdrdfdnkCfrdlPVAFNHKTKECIIIGTHEEKKTTNCSDNSRNNGR-CFSSIKKEKGKDW
Pb - M1    CfdrdfdnkCfrdlPVAFNHKTKECIIIGTHEEKKTKNCSDHSRNNGR-CFSSIKKEKGKDW
Pf - M1    ClykdfnnsCflnlPILFNHQTKECVH-GTHEEKRIHNCQSGSTDQNIQRCFLPVKKEKGNQW
YM - M2    ClenaynnkCfrslPAYFNHETNECIILGTHEQERNNNCRTRRSDTDKPNCQNVRKNISTKNW
Pb - M2    ClenaynnkCfrnlPAYFNHETKECVILGTHEQERVNDCRKRKEDINKPNCQDVRKTPLSKDW
Pf - M2    ClensfgnkCfrnlPAYYNHLTNECVILGTHEQERTNSCRRTKEEKKKPNCQILRKTTDSKDW YM - M1    TYASSFLRPDYETKCPPRYPLNNSEFGYFNYNTGNCES-PTKLYDNSVISFNECIEKLFnfny
Pb - M1    TYVSSFLRPDYETKCPPRYPLNNSEFGYFNYNTGKCES-PTKLYDNTVISFNQCIEKLFsfny
Pf - M1    TYASSFIRTDYMTKCPPRFPLNHTMFGYFNYSTG
YM - M2    TYVTSFIRPDYEEKCPPRYPLKFKSFGKYDEETGKCKSLINKKNIINIPLFSSCLE-YMfimy
Pb - M2    TYVTSFIRPDYEEKCPPRYPLKFKSFGKYDEATGKCKSLINKEYIIDIPWFASCLE-YMfims
Pf - M2    TYVSSFIRPDYETKCPPRYPLKSKVFGTFDQKTGKCKSLMDKAYEVGINKFSVCLE-YLflvs YM - M1    anedpeekrnnylwgvwvlgnkqnklnsMNDL-GVCALLKEKPTCVLKLQNYY
Pb - M1    anenpdqkrsnylwgvwvlenkqnkInsMNDL-GVCVLLKERPTCVLKKQNYY
Pf - M1
YM - M2    psvlqrtekkny-wgvwvasesvnssnlYNAK-GECYYINEKPNCVIDKVNHF
Pb - M2    pdvsqrsekkry-wgvwiadksvnssnlDEAK-GKCYYITEKPNCVIDKVNHF
Pf - M2    pkdlynsgrnny-wgiwaadhsvnenniIEIANGKCYHLVVKPTCVIDKENHF
```

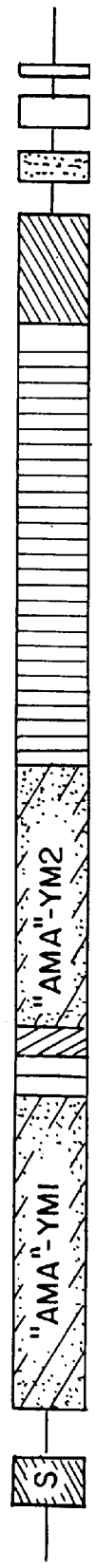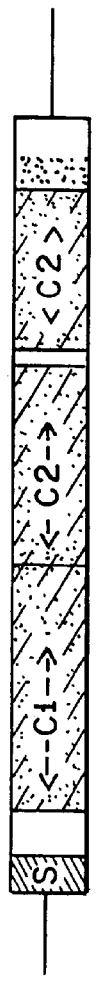
P. yoelii MAEBL
FIG. 2c
Plasmodium AMA-1
FIG. 2d

PLASMODIUM PROTEINS USEFUL FOR PREPARING VACCINE COMPOSITIONS

FIELD OF THE INVENTION

The present invention relates to a purified Plasmodium protein and method for vaccinating vertebrate species. More particularly, this invention is directed to a vaccine composition comprising an erythrocyte binding protein of a Plasmodium parasite (MAEBL), or fragment thereof for vaccinating against malaria infections.

BACKGROUND OF THE INVENTION

Malaria is an acute or chronic disease caused by the presence of sporozoan parasites of the genus Plasmodium in the host's red blood cells (erythrocytes). Four different species can cause the disease in humans: *Plasmodium faciparum, Plasmodium vivax, Plasmodium ovale* and *Plasmodium malariae*. Malaria merozoites (the vertebrate infective stage of the Plasmodium parasite) must attach to and invade a new erythrocyte in order to continue parasite development in the blood of an infected host. Symptoms of the disease (including shaking, chills, and fever) appear only when erythrocyte cells infected with the parasites rupture to release more parasites into the blood stream.

Plasmodium merozoites control invasion into erythrocytes by a series of molecular interactions. In particular, malaria parasites express Erythrocyte Binding Proteins (EBPs) during the invasive merozoite stage, and those EBPs interact with host cell surface proteins to facilitate host cell recognition and invasion. Determinants on human erythrocytes are essential for invasion of human erythrocytes by Plasmodium and much of current knowledge about malaria merozoite invasion of erythrocytes is based on observations of the primate malaria parasite *Plasmodium knowlesi* [Dvorak et al., Science 187: 748–750 (1975)]. *Plasmodium knowlesi* and *Plasmodium vivax* both require the presence of the Duffy blood group antigen in order to invade human erythrocytes [Miller et al., Science 189: 561–563 (1975) and Miller et al., N. Engl. J. Med. 295: 302–304 (1976)]; however, *Plasmodium falciparum* usually requires sialic acid-dependent epitopes on glycophorin A in order to invade human erythrocytes [Camus et al., Science 230, 553–6, 1985].

Merozoites interact with the erythrocyte by initially attaching at the point of first contact and then undergo apical reorientation. A junction then forms between the apical end of the merozoite and the erythrocyte, followed by vacuole formation and entry of the merozoite into the vacuole [Aikawa et al., J. Cell Biol. 77, 72–82 (1978)]. Junction formation and merozoite entry into the erythrocyte do not occur on erythrocytes lacking the appropriate receptor [Miller et al., J. Exp. Med. 149, 172–184 (1979)], indicating that a specific receptor is involved in apical junction formation but not initial attachment. Junction formation is the critical point of the invasion process when a parasite must commit itself to invade a particular cell, since subsequent steps appear non-reversible.

In *Plasmodium knowlesi, Plasmodium vivax* and *Plasmodium falciparum,* the principal invasion pathway uses a merozoite protein expressed from a homologous family of erythrocyte binding proteins (the EBP family) [Adams et al., Proc. Natl. Acad. Sci. USA 89, 7085–9, (1992)]. The EBP proteins are transmembrane proteins, characterized by two conserved cysteine-rich domains, and are expressed in the micronemes (an apical organelle thought to play a crucial role in host cell invasion) of invasive merozoites. The EBP family includes the *Plasmodium vivax/P. knowlesi* Duffy binding protein (DBP) family and the *P. falciparum* erythrocyte binding antigen-175 (EBA-175). In particular, The *P. vivax* and *P. knowlesi* Duffy antigen binding proteins bind to Duffy blood group antigens of human erythrocytes, and the *P. falciparum* erythrocyte binding antigen-175 (EBA-175) binds to sialic acid-dependent determinants on glycophorin A of human erythrocytes.

The EBP family has a common gene structure, including 4–5 exons encoding separate functional domains (signal, ligand, transmembrane cytoplasmic domains) and conserved codon usage at exon-intron boundaries. The genes are typically present in single-copy with the exception being *P. knowlesi* which has 3–5 genes. EBPs are expressed as transmembrane proteins in late schizont development and are located in the merozoite microneme. The encoded proteins have two characteristic conserved cysteine-rich domains [an amino cysteine-rich (region II) and carboxyl cysteine-rich (region VI) domain] separated by a hydrophilic region.

The cysteine-rich domains have a highly conserved core structure among Plasmodium species. Domains similar to the amino cysteine-rich domain of the DBP and the EBA-175 have been described in the *P. falciparum* var gene family. Var genes code for variant proteins (PfEMP-1) which are expressed on the surface of infected erythrocytes and mediate cytoadherence. The high conservation of the cysteine-rich domains suggests that they play a crucial role in host cell receptor recognition. This hypothesis was experimentally verified by showing that the amino cysteine-rich domain of the EBPs is the principal adhesion domain involved in receptor binding [Adams et al., Proc. Natl. Acad. Sci. USA 89, 7085–9, 1992; Chitnis et al., J. Exp. Med. 180, 497–506, 1994; Sim et al., Science 264, 1941–1944, 1994]. In particular, variation in the EBP region II has been correlated with differences in receptor recognition [Adams et al., Proc. Natl. Acad. Sci. USA 89, 7085–9, 1992; Chitnis et al., J. Exp. Med. 180, 497–506, 1994]. Region VI is a smaller, carboxyl domain that has no identified function, but is more highly conserved than region II.

*Plasmodium falciparum* merozoites are primarily dependent on a glycophorin A pathway for invasion of erythrocytes, but have the ability to develop or utilize an alternate invasion pathway when glycophorin A is absent [Pasvol et al., Nature 297, 64–6, 1982; Hadley et al., J. Clin. Invest. 80, 1190–3, 1987; Dolan et al., Acta Leiden 60, 93–9, 1991; Dolan et al., J. Clin. Invest. 86, 618–24, 1990; Dolan et al., Mol. Biochem. Parasitol. 64, 55–63, 1994; Perkins et al., Mol. Biochem. Parasitol. 27, 23–34, 1988]. The MAEBL protein disclosed herein represents a ligand of an alternate pathway of invasion for Plasmodium parasites.

MAEBL is a single-copy gene with a multi-exon structure like EBP, including conserved intron/exon boundaries. The carboxyl end of MAEBL is homologous to EBPs and the carboxyl cys-rich domain has approximately 50% identity with EBPs. A 50 amino acid tandem repeat spans the region between the cysteine domains, maintaining the equivalent spacing between the cysteine domains as in other EBPs. The putative ligand domain of MAEBL has identity to AMA-1 instead of the consensus DBL motif of EBPs. The MAEBL AMA-1-like regions are present as a tandem duplication (YM-M1, YM-M2) FIG. 2c analogous to the tandem DBL duplication found in *P. falciparum* EBL (EBA-175). (See FIG. 2d) The second copy of the AMA-1-like domain has greater identity to the AMA-1 consensus sequence. Differences between MAEBL and AMA-1 occur mostly in the loop regions between predicted disulfide bridges and includes an alternatively-spliced cryptic intron in YM-M2. Unlike AMA-1, the primary nucleotide sequences of the MAEBL AMA-1-like domains are poorly conserved, indicating a possible ancient and evolving gene origin parallel to the current AMA-1. MAEBL still retains amino acid sequence similarity to the part of the EBP molecule that connects to the merozoite (and likely transmits an internal signal associated with receptor recognition) thus indicating its equivalent but alternate role in receptor recognition.

SUMMARY OF THE INVENTION

Oligonucleotide primers matching the region encoding the carboxyl cysteine-rich domain of the EBA-175 were used in a polymerase chain reaction to identify homologous genes in the rodent malaria parasites P. berghei and P. y.yoelii, leading to the isolation of a P. berghei partial genomic clone and a single-copy gene in P. berghei that encode MAEBL. Antisera prepared against the carboxyl cysteine-rich domain of the rodent malaria MAEBL protein reacts with a 120 and 128 kDa protein doublet on Western blots of P. berghei parasite antigen and showed an apical localization pattern within merozoites by indirect immunofluorescence assays.

DNA sequences encoding Plasmodium MAEBL proteins have been isolated and cloned and used to express MAEBL proteins and peptide fragments. Compositions comprising those MAEBL protein or peptide fragments are used in accordance with the present invention to raise monoclonal and polyclonal antibodies against the Plasmodium MAEBL proteins. Furthermore the MAEBL protein or peptide fragments or DNA sequences encoding those proteins/peptides are used in accordance with the present invention to prepare vaccine compositions for administration to vertebrate species to prevent or enhance a cell's resistance to infection by the Plasmodium parasites or to alleviate the symptoms associated with the disease.

In one embodiment, the present invention relates to use of MAEBL as a vaccine for humans against malaria. The MAEBL DNA segment or a unique part thereof, or the MAEBL protein or a unique portion thereof, can be used to induce an immune response to the Plasmodium parasite thereby protecting the human against malaria. The MAEBL DNA segment can be used to express recombinant proteins or utilized to stably or transiently incorporate the MAEBL DNA segment into host cells by transformation or transfection to produce MAEBL proteins. Furthermore, synthetic MAEBL protein or unique peptide sequences derived from the MAEBL DNA segment or MAEBL amino acid sequences can also be prepared in accordance with the present invention.

BRIEF DESCRIPTION OF THE DRAWINGS

FIG. 1 is an alignment of the deduced amino acid sequences of the first (MI) and second (M2) AMA-1-like domains of P. y. yoelii YM (YM-M1=amino acids 26–423 of SEQ ID NO: 5 and YM-M2=amino acids 569–992 of SEQ ID NO: 5), P. berghei ANKA (Pb-MI=amino acids 27–423 of SEQ ID NO: 6, Pb-M2=amino acids 569–939 of SEQ ID NO: 6), and P. falciparum (Pf-M1=amino acids 1–253 of SEQ ID NO: 9; Pf-M2=amino acids 1–334 of SEQ ID NO: 8). The MAEBL AMA-1-like regions are present as a tandem duplication (YM-MI, YM-M2), and identity is greatest between the P. y. yoelii, P. berghei and P. falciparum AMA-1-like regions at the residues adjacent to cysteines in the first two cysteine loops of AMA-1, representing the core structure of the 44 kDa AMA-1 fragment. Conserved cysteine residues common to the MAEBL genes are boxed.

FIG. 2 shows schematic block diagrams: FIG. 2c of the P. yoelli MAEBL and FIG. 2d of the Plasmodium AMA-1 protein structures. The boxes represent exons, the solid boxes represent conserved EBP cysteine domains, the stippled boxes represent conserved AMA-1 cysteine motifs, the vertical striped box represents a region of repeat sequences and the "s" labeled boxes represent the signal peptide. The structure of MAEBL matches that of other EBP molecules, including the exon/intron junction boundaries of the 3' end of MAEBL.

DETAILED DESCRIPTION OF THE PREFERRED EMBODIMENTS

Figure 2A:
FIG. 2a of P. vivax DBP.

The study of adhesion molecules of human and simian malaria parasites is hindered by limited availability of parasite-derived proteins and the limited availability of primates for in vivo experimental studies. Accordingly, homologous EBPs in rodent malaria parasites were identified and characterized to assist in the isolation of human malaria parasite adhesion molecules and the preparation of vaccines against human malaria parasites.

The present invention is directed to the isolation and characterization of nucleic acid sequences that encode a new family of Plasmodium adhesion proteins referred to herein as MAEBL. More particularly, the present invention relates to nucleic acid sequences that encode at least a portion of a MAEBL protein, and the proteins/peptide fragments encoded by those sequences. The DNA sequences used in accordance with the present invention comprise substantially pure nucleic acid sequences isolated from Plasmodium parasites including *Plasmodium falciparum, Plasmodium vivax, Plasmodium ovate, Plasmodium berghei, Plasmodium y. yoelii, Plasmodium chabaudi, Plasmodium vance*, and *Plasmodium malariae*.

In accordance with one embodiment of the invention, a substantially pure nucleic acid sequence is described comprising a twenty base pair nucleotide portion identical in sequence to a consecutive twenty base pair portion of the sequences as set forth in the DNA sequence of SEQ ID NO: 1, 2, 3 or 4. In one embodiment the DNA sequence comprises a sequence selected from the group of sequences as set forth in SEQ ID NO: 1, 2, 3 or 4. Compositions comprising these substantially pure Plasmodium DNA sequences can be used in accordance with the presence invention as vaccines.

The Plasmodium MAEBL encoding sequences of the present invention can be inserted into commercially available DNA vectors (expression vectors) to express the encoded gene protein product. The expression vectors have promoter sequences and other regulatory sequences necessary for expression in host cells. The technique of using expression vectors to introduce exogenous genes and express their protein products in a host cell is well known to those familiar with the art. For example the expression vector pET21a is commercially available and can be used to express proteins in *E. coli*. Alternatively the protein can be expressed in a eukaryotic cell, such as yeast, using Pichia expression vectors (i.e. pHIL-D2) commercially available from Invitrogen. The Baculovirus system is also commercially available and can be used to express the MAEBL genes in insect cultures.

Once the MAEBL gene or fragment thereof has been cloned into an expression vector, the resulting vector can be used to transform a host cell, using procedures known to those familiar with the art. Such transformation procedures include but are not limited to microinjection, mircoprojectile bombardment, electroporation, calcium chloride premeablization, polyethylene glycol permeabilization, protoplast fusion or bacterial mediated mechanisms such as *Agrobacterium tumafaciens* or *Agrobacterium rhizogenes*.

Host cells may be selected from any cell in which expression of modified proteins can be made compatible, including bacteria, fungus, yeast, plant cells and animal cells. Suitable host cells include prokaryotes selected from the genus Escherichia or Staphylococcus and eukaryotes selected from the genus Pichia (including *Saccharomyces cervisae*, for example). In addition, mammalian cell culture (such as CHO and COS cells) can be used to express the MAEBL proteins and protein fragments.

The transformed host cells synthesize the MAEBL protein or peptide fragment which can be isolated and purified using standard methods known to those familiar with the art. In one embodiment the MAEBL proteins and peptide fragments can be expressed as fusion proteins to assist in the purification of the MAEBL protein products.

The present invention is also directed to a substantially purified polypeptide comprising an amino acid sequence selected from the group of sequences as set forth in SEQ ID NO: 5, 6, 7, 8 and 9. In one embodiment the polypeptide comprises an amino acid sequence having a consecutive 10 amino acid sequence identical with a consecutive 10 amino acid sequence selected from the group of sequences as set forth in SEQ ID NO: 5, 6, 7, 8 and 9. In one embodiment, in accordance with the present invention, the composition comprises a peptide having the sequence as set forth in SEQ ID NO: 10, 11, 12, 13, 14 or 15. The present invention also relates to a substantially purified DNA sequence that encodes a MAEBL polypeptide or peptide fragment. Accordingly, the present invention relates to DNA sequences encoding MAEBL, recombinant DNA constructs that comprise sequences encoding MAEBL and to recombinately or synthetically produced MAEBL proteins or peptide fragments thereof.

The MAEBL gene product of Plasmodium parasites is involved in erythrocyte binding and invasion of the Plasmodium parasite into host blood cells. The mammalian proteins have two consensus motifs including an amino domain and a carboxy domain. The amino domain can be divided into two AMA-1-like cysteine-rich motifs. These cysteine-rich motifs are highly conserved within the various species of Plasmodium parasites. These proteins are also present on the cell surface and thus provide an excellent candidate for preparing vaccine compositions.

In accordance with one embodiment of the present invention antibodies are provided that are specific for epitopes present on the MAEBL proteins of the Plasmodium parasites. Thus in one embodiment, the present invention relates to a purified form of an antibody (monoclonal or polyclonal) specific for a MAEBL protein. More particularly, the antibodies are directed to the conserved regions of the MAEBL proteins and more preferably to the AMA-1-like cysteine-rich motifs of the MAEBL proteins. One skilled in the art, using standard techniques well known to those skilled in the art can raise antibodies to the proteins and peptide fragments disclosed in the present invention. These antibodies can be useful as diagnostic agents or can be utilized as therapeutic agents for treating or preventing malaria.

In accordance with the present invention, a vaccine composition for use in preventing malaria infections in humans is provided. In one embodiment the vaccine composition comprises a MAEBL protein and a pharmaceutically acceptable carrier. As one skilled in the art will readily understand it is not necessary to use the entire MAEBL protein; a unique portion of the protein (for example a synthetic polypeptide corresponding to a conserved region of the MAEBL protein) can be used in formulating a vaccine composition. Thus a vaccine composition against malaria in accordance with the present invention comprises all of, or a unique portion, of a MAEBL protein, in an amount sufficient to induce immunization against the Plasmodium parasite, and a pharmaceutical acceptable carrier.

In one embodiment the composition comprises a polypeptide and a pharmaceutically acceptable carrier thereof, wherein the polypeptide comprises an amino acid sequence that encodes an AMA-1-like domain of a MAEBL protein. The second AMA-1-like domain of the MAEBL proteins is one preferred portion of the MAEBL protein utilized as an antigenic fragment for generating antibodies to the MAEBL proteins and for use in vaccine compositions. In another embodiment, the polypeptide of the vaccine composition comprises an amino acid sequence that encodes at least a consecutive 6 amino acid portion of an AMA domain of a MAEBL protein. For example, the amino acid sequence is selected from the group of peptide sequences as set forth in SEQ I.D. NO: 9, 10, 11, 12, 13 and 14.

Pharmaceutically acceptable carriers commonly used in vaccines can be used to deliver the protein or peptide to an organism in need of treatment. Such carriers include MTP, tetnus toxoid or liposomes. Furthermore, vaccines of the present invention can also include effective amounts of immunological adjuvants known to enhance an immune response. Such adjuvants include IL-2 and alum and are well known to those skilled in the art.

The protein or polypeptide is present in the vaccine in an amount sufficient to induce an immune response against the antigenic portion and thus to protect against a Plasmodium infection. Protective antibodies are usually best solicited by a series of two to three doses given about two to three weeks apart. However administration of the vaccine composition in accordance with this invention can be affected in a single or multiple dose protocol. Furthermore, additional dosages can be administered when concentrations of circulating antibodies in the human drops.

The present invention further relates to a receptor blocking therapy which disrupts the life cycle of the parasite in humans. Antibodies specific for the MAEBL protein or a unique portion thereof, or for the receptor binding site of the MAEBL ligand may be administered to interfere with parasite ligand-host receptor interaction, thus decreasing the parasites ability to invade erythrocytes. Alternatively, the erythrocyte or other host receptors recognized by the MAEBL proteins may be administered to a human to disrupt parasite life cycle to enhance resistance to a Plasmodium infection.

The major human malaria parasite, *P. falciparum* has redundant or alternate receptor-ligand pathways of invasion. Therefore, an effective vaccine for blocking parasite invasion of erythrocytes by *P. falciparum* malaria, will also target the redundant receptor ligand interactions that occur during the invasion process. Thus in one embodiment, the present vaccine compositions comprise a MAEBL polypeptide in combination with additional Plasmodium specific proteins or peptide fragments. For example, the second polypeptide may comprise an amino acid sequence that encodes a Duffy binding protein or erythrocyte binding antigen-175 of a malaria Plasmodium parasite. As described above the Duffy protein is one member of the EBL family of proteins that are utilized by Plasmodium parasites to invade erythrocytes. Thus, one vaccine composition in accordance with the present invention comprises two or more polypeptides (or polypeptide fragments) and a pharmaceutically acceptable carrier, wherein at least one polypeptide (or polypeptide fragment) is a MAEBL protein and another polypeptide (or polypeptide fragment) is EBA-175. EBA-175 and the Duffy binding proteins of Plasmodium parasites have been described in the prior art as well as their use in preparing vaccines to prevent malaria infections. See U.S. Pat. No. 5,198,347 the disclosure of which is expressly incorporated herein by reference.

The present invention also relates to a method of vaccinating a vertebrate species against a malaria Plasmodium parasite. The method comprises the steps of administering a vaccine composition comprising a protein or peptide fragment of a Plasmodium EBP wherein the peptide comprises at least a consecutive six amino acid sequence that is identical to a six amino acid sequence selected from the groups consisting of the sequences as set forth in SEQ ID NO: 5, 6, 7, 8 and 9, and a physiologically acceptable carrier. In one embodiment the vaccine composition further comprises a second protein or peptide fragment wherein the second protein or peptide fragment comprises the erythrocyte binding antigen-175 of an erythrocyte binding protein. The vaccine composition also can include various adjuvants known to those skilled in the art. The vaccine composition can be administered to a vertebrae species either orally or intraperitoneally using techniques well known to those skilled in the art.

In yet a further embodiment, the present invention relates to a method of disrupting the Plasmodium life cycle in humans by administering antibodies specific for the binding site of MAEBL in an amount sufficient to inhibit the parasite protein from binding red blood cells in the human.

EXAMPLE 1

Isolation of EBP Homologues

Materials and Methods

Parasites, DNA and RNA preparation. ICR mice were inoculated intraperitoneally with cloned lines of P. y. yoelii YM, BALB/c mice were inoculated with P. y. yoelii 17X, P. berghei ANKA, and P. v. Vance, C57/BL6 mice were inoculated with P. c. chabaudi Aj. To isolate genomic DNA, parasitized blood was collected from infected animals when the hematocrit began to drop significantly (<40%) and extracted by a chloroform phenol method. Total RNA was isolated using the ULTRASPEC RNA isolation system (BIOTECX laboratories, Houston, Tex.).

Gene Identification. The region encoding the carboxyl cysteine-rich domain of the EBPs (3' region) was chosen as a target because it shows the highest degree of interspecies sequence conservation. Oligonucleotide primers based on the coding sequence of the P. falciparum EBA175 3' region (143 sense, SEQ ID NO: 17: AAATGTGAGAAC-GAAATTTCTGTAAAATATTG; 142 antisense, SEQ ID NO: 18: GGATCATCAAATTCCCTTTTCGTAC) were used to PCR amplify this region from P. berghei ANKA and P. y. yoelii YM genomic DNA. The polymerase chain reaction used amplification conditions that permitted primer-template mismatches. The reaction mixtures contained 10 mM Tris-HCl (pH 8.3), 50 mM KCl, 1.5/3-0 MM M9C12, 200 mM each dNTP, 2.5 units Taq Polymerase, 600 ng of each oligonucleotide and 100 ng template DNA in a final volume of 100 μl. The reactions were subjected to: one cycle of 45 s at 94° C.; 5 cycles of 30 s at 94° C., 2 min at 42° C., 1 min at 74° C.; and 35 cycles of 30 s at 94° C., 45 s at 42° C. and 1 min at 74° C. The amplified fragments were sequenced by the dideoxy chain termination method directly (BRL) or were cloned into plasmid pCRII (Invitrogen) and then sequenced (Amersham).

Southern blot analysis. Genomic DNA of p. y. yoelii YM, P. y. yoelii 17X, P. berghei ANKA, P. c. chabaudi Ai and P. v. Vance digested with restriction enzymes EcoRI or EcoRV, was separated by agarose gel electrophoresis, fragmented in 0.25 M HCl, denatured in 0.5 M NaOH/1.5 M NaCl and blotted onto GeneScreen Plus (Du Pont) in 20×SSC (1×SSC is 150 mM NaCl, 15 mM sodium citrate, pH 7.0). The membrane was baked for 2 h at 80° C. in a vacuum. A PCR amplified fragment from the P. y. yoelii YM 3' region was radiolabeled by a random priming reaction using the Klenow fragment of DNA polymerase I according to the manufacturer's instructions (BRL). The membrane was prehybridized in 6×SSC/20 mM $Na_2HPO_4$ (pH6.8)/5×Denhardt's solution/0.5% SDS/100 mg $ml^{-1}$ heparin for 2 h at 60° C. and then probed overnight. The blot was then incubated in a final wash of 2×SSC/0.5% SDS at 60° C. and the membrane exposed to a DuPont NEF-496 film for 48 h at −70° C. Genomic DNA of P. berghei was fragmented with restriction endonuclease HindIII, separated and blotted as described. A synthetic oligonucleotide based on the sequence of the P. berghei 182 bp fragment (159 antisense, SEQ ID NO: 19: aggatccAATAATCTGATATTGAGCAGCATAATTGTTTC) was radiolabeled using T4 polynucleotide kinase (BRL) and used as a probe. Hybridization conditions were the same as described above except that hybridization was done at 45° C. and the final wash was done in 6×SSC/0.5% SDS at 50° C.

Construction and screening of a P. berghei genomic DNA library. Genomic DNA of P. berghei was digested with HindIII, size fractionated on a NaCl/sucrose gradient and the 9–12 kb fraction was ligated into plasmid pUC8. This fraction was selected based on size estimates from Southern blot data. Ligations were transformed into E. coli TG2 electrocompetent cells by electroporation. Plasmid was reisolated from the library and pools were tested by PCR with oligonucleotides 142/143. Positive pools were transformed into E. coli TG2 cells. Colony lifts were done on MAGNA LIFT nylon membranes (Micron Separations) and these lifts were screened with radiolabeled oligonucleotide 159 under the same conditions as described for Southern blot hybridizations.

Cloning of the 3' region of other rodent malaria species. Oligonucleotide primers based on the sequence of a P. berghei genomic clone encoding the complete carboxyl cysteine-rich domain (205 sense, SEQ ID NO: 20: gaag-gatccAATTATGAAACGCGCCATATTG; 206 antisense, SEQ ID NO: 21: cttgaattcaagcttCTTGAATATTC-CTCTTTACTAAAG; bases shown in lower case were added to facilitate directional cloning into plasmid pGEX-2T [Smith et al., Current protocols in molecular biology 2, 16.7.1–8, 1991], the restriction cleavage sites are in italics) were used to amplify the complete 3' region from genomic DNA of P. y. yoelii YM, P. y. yoelii 17X, P. c. chabaudi Ai and P. v. Vance.

DNA sequencing and sequence analysis. The PCR products were cloned into plasmid pCRII (Invitrogen) and both strands from different clones were completely sequenced by the dideoxy chain termination method (Pharmacia Biotech). Nucleic acid and deduced amino acid sequences were aligned using the ALIGNMENT algorithm (Geneworks 2.2, Intelligenetics).

Detection of expression and capture of a 3' cDNA. Total RNA of P. berghei was treated with DNase I (Gibco BRL)

and used as template in reverse transcriptase (RT)-PCR reactions (Perkin Elmer) with the oligonucleotide primers (302 sense, SEQ ID NO: 22: GAAACAATTATGCTG-CAATATCAGATTATT; 313 antisense, SEQ ID NO: 23: CATATTTTGTGTTGTATAAAC). Oligonucleotide primer 302 was located within the 3' region encoding the carboxyl cysteine-rich domain, oligonucleotide primer 313 was made based on the sequence of the predicted 3' UTR of the *P. berghei* genomic clone.

Results

Gene identification by PCR. A polymerase chain reaction used oligonucleotides based on the sequence of the *P. falciparum* EBA-175 3' region in amplification conditions that permitted primer-template mismatches. A 182 bp fragment was PCR amplified from both *P. berghei* and *P. y. voelii* YM genomic DNA that was similar in size to the 3' fragment amplified from *P. falciparum* genomic DNA. This 182 bp fragment was consistently amplified with different $MgCl_2$ concentrations from *P. berghei* genomic DNA, but only the less stringent PCR reaction conditions permitted amplification of this fragment with *P. y. yoelii* YM genomic DNA. Three additional larger-sized fragments were consistently amplified from *P. y. yoelii* YM genomic DNA. Sequence analysis of all amplified fragments showed that only the 182 bp PCR fragments shared significant deduced amino acid sequence identity to known EBPs.

Isolation of a *P. berghei* gene fragment encoding the carboxyl cysteine-rich domain. An oligonucleotide (159) was synthesized based on part of the nucleotide sequence of the *P. berghei* 182 bp PCR fragment. A clone that hybridized strongly with the oligonucleotide 159 and contained a 1.6 kb genomic fragment (although the genomic fragments were initially size-selected for 9–12 kb) was isolated from a *P. berghei* genomic library. The instability of the cloned fragment appeared to be due to an extended repeat sequence upstream of the 3' region as the cloning site in the polylinker at the 5' end of the insert was lost in addition to this part of the genomic fragment. The nucleotide sequence of the 182 bp PCR fragment was identical to part of a 323 bp region of this clone. Sequence analysis showed that this 323 bp region had high deduced amino acid sequence identity to the carboxyl cysteine-rich domains of the *P. vivax/P. knowlesi* DBPs FIG. 2a and *P. falciparum* EBA-175 (FIG. 2b) (54%/48% and 47% identity, respectively). Outside this domain no significant sequence similarity was identified.

The EBP carboxyl cysteine-rich domain is conserved in malaria parasites. Two oligonucleotides based on the *P. berghei* 3' region nucleotide sequence were used to amplify the homologous regions from *P. y. yoelii* YM, *P. y. yoelii* 17X, *P. c. chabaudi* AJ and *P. v. Vance* genomic DNA. Fragments of 323 bp were amplified from all species. Deduced amino acid sequence comparison of these fragments showed a high degree of identity among them (>80% identity) All 8 cysteine residues, the principal characteristic for the carboxyl cysteine-rich domain, were conserved in each species, such that a consensus sequence could be generated as represented by SEQ ID NO: 16. Comparison of the carboxyl cysteine-rich domains of rodent malaria parasites to those of the *P. vivax/P. knowlesi* DBPs and the *P. falciparum* EBA-175 showed an overall amino acid identity of 29%.

The 3' region is present in a single copy gene. Southern blot hybridizations of *P.y. yoelii* YM, *P.y. yoelii* 17X, *P. berghei* ANKA, *P. c. chabaudi* AJ and *P. v. vinckei* identified a single EBP in each species. Genomic DNA fragmented with restriction endonucleases EcoRV or EcoRI were hybridized with the *P. y. yoelii* YM 3' region. In each species a single restriction fragment hybridized to the probe. This was confirmed with other restriction endonucleases (HindIII, BamHI, HaeIII) and by using oligonucleotide 159 as a probe. Restriction fragment-length polymorphisms (RFLP) were seen among the species; however, no restriction fragment length polymorphisms (RFLP) could be detected for the 17X and YM clones of *P. y. yoelii*.

Figure 2B:
FIG. 2b of P. falciparum EBA 175.

The carboxyl cysteine-rich domain is expressed as part of a putative transmembrane protein in *P. berghei*. Reverse transcriptase (RT)-PCR with the oligonucleotides 302/313 amplified a 353 bp fragment from *P. berghei* total RNA, demonstrating the presence of an EBP transcript in blood forms of the parasite. No amplification was detected in control reactions without RT. A PCR reaction with oligonucleotides 302/313 and with *P. berghei* genomic DNA as a template amplified a 756 bp fragment. Sequence comparison of the 353 bp RT-PCR fragment with the sequence of the *P. berghei* genomic clone and the 756 bp genomic PCR fragment allowed the elucidation of the exon/intron structure (See FIG. 2c). The carboxyl cysteine-rich domain is followed by an intron of 97 nucleotides. The next exon encodes a domain of 26 amino acids showing structural features consistent with a transmembrane domain. A Kyte-Doolittle hydrophobicity plot predicted a minimum of 18 continuous hydrophobic residues within this exon. This putative transmembrane domain is followed by an intron of 129 nucleotides. The next two exons encode a putative cytoplasmic domain and are separated by an intron of 126 nucleotides. The second exon of the putative cytoplasmic domain encodes the last four amino acids of the protein. The position of the exon boundaries within a codon for all three splice junctions is homologous to the EBA-175 and the DBPs (FIG. 2a).

EXAMPLE 2

Preparation of glutathione s-transferase (GST) fusion proteins. GST fusion proteins of both the *P. y. yoelii* YM and *P. berghei* ANKA carboxyl cysteine-rich domains were prepared. The PCR-products generated with oligonucleotides described in Example 1 were inserted in frame into plasmid pGEX-2T. Transformants were screened for correct insert orientation by restriction with the appropriate enzyme (s). Fusion proteins were purified on Glutathione Sepharose 4B (Pharmacia) and eluted with reduced glutathione.

Polyclonal Serum Preparation and Indirect Immunofluorescence Assay. Approximately 1.0 mg of each fusion protein, emulsified in Freund's complete adjuvant (FCA), was injected subcutaneously into rabbits. Animals were boosted 4 times at 2 week intervals with 1.0 mg of each fusion protein in Freund's incomplete adjuvant (FIA). Serum reactivity was checked against the fusion protein by western blot, ten days after each boost. For Indirect Immunofluorescence Assays (IFA), *P. y. yoelii* YM, *P. y. yoelii* 17X, *P. berghei* ANKA, *P. c. chabaudi* Ai, and *P. v. vinckei* blood stage parasites were harvested, washed 3× in RPMI 1640 medium, 3× RPMI 1640 containing 0.1% saponin and 0.1% fetal bovine serum (buffer) and then incubated with the appropriate primary antibody diluted 1:200 in buffer for 10 minutes, at 37° C., agitating occasionally. Parasites were washed once in buffer and then incubated with fluorescein-conjugated goat anti-rabbit IgG (Kirkegaard & Perry), diluted 1:10 in buffer, at room temperature for 10 minutes, mixing continuously. The parasites were washed once more in buffer and mounted in 0.85% saline containing 10% glycerol and 0.1% p-phenylenediamine on poly-L-lysine coated coverslips. Samples were viewed under a MRC-1024 Laser Scanning Confocal Imaging System (Bio Rad), using 10% laser power.

Antigen Preparation and Western Blot. *P. berghei* ANKA antigen was prepared by passing infected rat erythrocytes through a leukocyte removal column (Baxter) and washing the cells in RPMI 1640. A fraction enriched in schizonts was isolated using a 45% percoll (Pharmacia) step gradient, centrifuged 5 min at 1300 g. After collection, this fraction was washed 3× in RPMI 1640, lysed in 10 volumes of Buffer H [5 mM Tris base (pH 7.5), 5 MM sodium azide, 5 mM magnesium chloride, 1 mM dithiothreitol, 1 mM EGTA, and 0.5 mM PMSF] and centrifuged 5 min at 20,000×g. The pellet was washed twice more in Buffer H, resuspended in Buffer H and stored at –80° C. SDS-PAGE sample buffer (50 MM Tris base, 5% Sodium Lauryl Sulfate (Sigma, catalog #S529500), 20% glycerol and 5% 2-mercaptoethanol) was added to resuspended pellets before thawing. Proteins were separated by SDS-PAGE (7.5% acrylamide) and transferred to nitrocellulose. Western blot strips blocked in 1% gelatin were incubated for 90 min in antibodies preadsorbed to uninfected mouse erythrocyte ghosts (prepared using the method above, excluding the percoll step gradient) and GST bound to Glutathione Sepharose 4B. Blots were washed 5× in PBS containing 0.05% Tween (PBS-T) and then incubated in alkaline phosphatase-conjugated secondary antibody (Promega) for one hour. Blots were washed 5× in PBST and developed in NBT/BCIP (Promega).

Results

Immunodetection of the EBP homologies. The carboxyl cysteine-rich domains of *P. berghei* and *P. y. yoelii* YM were expressed as GST fusion proteins and used to produce polyclonal anti-*P. berghei* (anti-PB2T/1) and anti*P. y. yoelii* YM (anti-YM2T/8) rabbit antisera. Western blot of a lysed schizont-enriched insoluble fraction from *P. berghei* parasites. Strips were reacted to (1) *P. berghei* ANKA post-infection rat immune serum, (2) polyclonal rabbit serum to the carboxyl cysteine-rich domain of *P. berghei* (anti-PB2T/1) and (3) preimmune rabbit serum collected prior to immunization with the carboxyl cysteine rich domain of *P. berghei*. The anti-PB2T/1 serum detected two closely migrating proteins of 120 and 128 kDa on western blots of schizont-enriched *P. berghei* antigen. These proteins were only found in the insoluble fraction of parasite lysates and the doublet was only resolved when the antigen was prepared in SDS PAGE sample buffer containing twice the normal concentration of a mixedlength SDS. These results were confirmed by immunoprecipitation of similar sized proteins from the insoluble fraction of radiolabeled *P. berghei* schizonts and mixed-stage parasites. This is consistent with the genetic data, identifying the *P. berghei* EBP as a transmembrane protein. The 120 and 128 kDa proteins were not detected with preimmune sera nor antibodies reactive with AMA-1. Relative molecular masses (Mr) were calculated relative to the reported apparent molecular masses of standards (BRL); myosin (207,000), phosphoylase b (107,000), bovine serum albumin (68,000), and ovalbumin (46,000).

The anti-YM2T/8 serum reacted strongly to *P. y. yoelii* YM schizonts and crossreacted strongly with *P. y. yoelii* 17X, *P. berghei*, and *P. v. vinckei* parasites, while weaker crossreactivity was seen on all parasites except *P. chabaudi* AJ, which displayed a more diffuse cytoplasmic fluorescence pattern, with a few areas of higher intensity. Merozoite surface fluorescence can be seen on both *P. y. yoelii* YM and *P. y. yoelii* 17X parasites. The A7 antisera to the AMA-1-like domain gave a similar, but more diffuse localization pattern as antisera to the carboxyl EBP cysteine domain; however, the recombinant AMA-1-like domains were poorly immunogenic generated lower titer antisera. The *P. c. chabaudi* schizonts had a diffuse cytoplasmic fluorescence with fewer areas of high intensity immunofluorescence. The prebleed sera did not react with the parasite with *P. c. chabaudi* parasites.

EXAMPLE 3

Recombinant MAEBL Proteins Bind Erythrocytes

The AMA-1-like domains of MAEBL act as a ligand that binds erythrocytes. DNA segments of MAEBL were expressed as recombinant HSV gD1 fusion proteins on the surface of transfected COS7 cells in vitro [Chitnis et al., J. Exp. Med. 180, 497–506, 1994; Sim et al., Science 264, 1941–1944, 1994]. Erythrocytes bound specifically to cells transfected with the MAEBL DNA segments encoding the AMA-1 like domains. These experiments defined the ligand domain of MAEBL and also identified the ligand domain of AMA-1.

Recombinant plasmid constructs for surface expression. The AMA-1-like coding sequences of MAEBL were expressed in cell monolayers as transmembrane fusion proteins with HSVgD1. The eukaryote expression plasmid pRE4 was engineered to produce these fusion proteins with the AMA-like domains subunits YM-M1 and YM-M2. Both YM-M1 and YM-M2 were assayed separately since the second and not the first DBL domain of the tandem repeat of *P. falciparum* EBA-175 can mediate receptor binding.

There are no PvuII nor ApaI restriction sites in any of the target sequences to be cloned, so all of the plasmodial sequences were inserted at these sites of the HSVgD-1 coding sequence. The MAEBL protein sequence started in the first block with sequence identity to AMA-1 at residues NPQED . . . (oligonucleotide 297) for YM1 and NPQAE . . . (oligonucleotide 293) for YM2; the expressed segments ended at residues . . . YFDNN (oligonucleotide 293) for YM1 and . . . NDIDF (oligonucleotide 301) for YM2, respectively.

Transfection for cytoadherence assays: COS7 (ATCC 1651) monolayers seeded at $5 \times 10_4$ cells/well in 4-well chamber slides were incubated in S-DMEM (10% Fetal Bovine Serum or Newborn Calf Serum in DMEM) 24 hr at 370 C. in 5% $CO_2$ until 40–60% confluence; washed in DMEM; incubated with 250 µl of 4 µg/ml of purified plasmid DNA (Maxi Prep, Qiagen) in 10% Lipofectin (BRL), DMEM 24 hr; and replace transfection media and incubate with S-DMEM 48–72 hr at 37° C. in 5% $CO_2$.

Cytoadherence assay. Erythrocyte cytoadherence was assayed 48 hr after transfection. Erythrocyte binding assays used washed cells from outbred ICR adult mice, the strain used maintain *P. berghei* ANKA and *P. yoelii* YM. Monolayers were washed with DMEM, 250 µl of 1% suspension of washed erythrocytes are added to each chamber, incubated for 2 hr at 37°, washed 3× with DMEM to remove non adherent erythrocytes, and examined by inverted phase microscopy for rosettes of erythrocytes attached to transfected cells.

EXAMPLE 4

Isolation of Genomic DNA Encoding MAEBL

Parasites, DNA and RNA preparation. ICR mice were inoculated intraperitoneally with cloned lines of *P. y. yoelii* YM, BALB/c mice were inoculated with *P. y. yoelii* 17X, *P. berghei* ANKA, and *P. vinckei vinckei*, C57/BL6 mice were inoculated with *P. chabaudi chabaudi* AJ. To isolate genomic DNA, parasitized blood was collected from infected animals when the hematocrit began to drop significantly (<40%) and extracted by a chloroform phenol method. Total RNA was isolated using the ULTRASPEC RNA isolation system (BIQTECX laboratories, Houston, Tex.).

Isolation of MAEBL gene fragments. Oligonucleotide 159 was synthesized based on the nucleotide sequence of the *P. berghei* and *P. yoelii* 182 bp PCR fragments and was used to identify MAEBL gene elements.

Construction and screening of a *P. berghei* genomic DNA library. Genomic DNA was digested with HindIII, size fractionated on a NaCl/sucrose gradient and the 9–12 kb fraction was ligated into plasmid pUC8. This fraction was selected based on size estimates from Southern blot data. Ligations were transformed into *E. coli* TG2 electrocompetent cells by electroporation. Plasmid was reisolated from the library and pools were tested by PCR with oligonucleotides 142/143. Positive pools were transformed into *E coli* TG2 cells. Colony lifts were done on MAGNA LIFT nylon membranes (Micron Separations) and these lifts were screened with radiolabeled oligonucleotide 159 by Southern blot hybridizations done at 45° C. and the final wash was done in 6×SSC/0.5% SDS at 50° C.

Construction and screening of a *P. yoelii* genomic DNA libraries. A *P. yoelii* genomic library was prepared from EcoRl-digested genornic DNA ligated into pCDNAIII (Invitrogen). A *P. yoelii* MAEBL genomic clone was isolated based on the clone's high affinity for the oligonucleotide 159. The total genomic frament cloned was 9 kb in size and the previously isolated 182 bp PCR fragment was identical in sequence to part of a 323 bp region of this genomic clone.

Sequence analysis showed that the 323 bp region had a high deduced amino acid sequence identity to the carboxyl cysteine-rich domains of the *P. vivax/P. knowlesi* DBPs and *P. falciparum* EBA-175 (54%/48% and 47% identity, respectively. Outside this domain no significant sequence similarity was identified. This clone was then used to isolate a 5 kb clone from a cDNA library prepared from *P. yoelii* polyA-enriched RNA. This clone contained both AMA-1-like domains, the start codon and a 1.5 kb 5' untranslated region.

The nucleotide sequence (SEQ ID NO: 1) and deduced amino acid sequence (SEQ ID NO: 5) of *Plasmodium yoeli* YM MAEBL were assembled from genomic and cDNA clones and polymerase chain reaction-amplified products derived from genomic DNA and reverse-transcribed transcripts.

Nucleotide sequence (SEQ ID NO: 2) and deduced amino acid sequence (SEQ ID NO: 6) of part of the *Plasmodium berghei* ANKA 5' MAEBL AMA-1-like sequence were assembled from genomic and cDNA clones and polymerase chain reaction-amplified products derived from genomic DNA and reverse-transcribed transcripts.

Nucleotide sequence (SEQ ID NO: 3) and deduced amino acid sequence (SEQ ID NO: 7) of the *Plasmodium berghei* ANKA 3' MAEBL EBP carboxyl domain were assembled from genomic and cDNA clones and polymerase chain reaction-amplified products derived from genomic DNA and reverse-transcribed transcripts.

Nucleotide sequence (SEQ ID NO: 4) and deduced amino acid sequence (SEQ ID NO: 8 and SEQ ID NO: 9) of *Plasmodium falciparum* MAEBL were assembled from clones of polymerase chain reaction-amplified products derived from genomic DNA.

What is claimed is:

1. An isolated polypeptide comprising the amino acid sequence as set forth in SEQ ID NO: 8.

2. An isolated amino acid sequence comprising a peptide sequence selected from the group consisting of the sequences as set forth in SEQ ID NO: 10, SEQ ID NO: 11, SEQ ID NO: 12, SEQ ID NO: 13, SEQ ID NO: 14 and SEQ ID NO: 15.

3. An immunogenic composition comprising an isolated polypeptide and a pharmaceutically acceptable carrier, wherein said polypeptide comprises an amino acid sequence that includes a MAEBL protein cysteine domain (SEQ ID NO: 8).

4. The immunogenic composition of claim 3 further comprising a second polypeptide, said second polypeptide comprising an amino acid sequence that includes at least a portion of a Duffy antigen binding protein or EBA-175 protein of a malaria Plasmodium parasite.

5. The immunogenic composition of claim 3 wherein said polypeptide comprises a peptide sequence selected from the group consisting of the sequences as set forth in SEQ ID NO: 10, SEQ ID NO: 11, SEQ ID NO: 12, SEQ ID NO: 13, SEQ ID NO: 14, and SEQ ID NO: 15 and a pharmaceutical acceptable carrier.

6. An immunogenic composition comprising a polypeptide and a pharmaceutically acceptable carrier, wherein said polypeptide comprises an immunogenic amino acid sequence that includes at least a consecutive 6 amino acid fragment of a cysteine domain of a MAEBL protein (SEQ ID NO: 8) selected from the group consisting of the sequences as set forth in SEQ ID NO: 10, SEQ ID NO: 12, SEQ ID NO: 13, and SEQ ID NO: 15.

* * * * *

UNITED STATES PATENT AND TRADEMARK OFFICE
CERTIFICATE OF CORRECTION

PATENT NO.    : 6,120,770
DATED         : September 19, 2000
INVENTOR(S)   : Adams et al.

It is certified that error appears in the above-identified patent and that said Letters Patent is hereby corrected as shown below:

<u>Column 1,</u>
Line 5, please insert -- This invention was made with U.S. Government support under Grant No. AI33656 awarded by the National Institutes of Health. The U.S. Government has certain rights in the invention. --

Signed and Sealed this

Fifteenth Day of April, 2003

JAMES E. ROGAN
*Director of the United States Patent and Trademark Office*

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 5433 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Plasmodium yoelii (xi) SEQUENCE DESCRIPTION: SEQ ID NO:1:

```
GCGGGTGTGT TTCATTTATT CTGCATCATT GCATATTATA TGCATATTTT TTAATTGATA      60

AATGTAAAGA GTCAATTGAA TTGATTTGTA GATATATACT ATATTAATAT ATAAATATTT     120

TCAATTATTA CAATAATATA AAGTATGAAG ATATATCATA ACATTTTTGG ATTCTGCATT     180

TTTATATCCT TATGGACTCC TTCTATACGA GCTATAGATA ACCCACAAGA AGATTTTATG     240

GACAGATTTG ATATCCTAAA TAACCATGTA AATATAAAAT GGACGAACTC AGGATCATTA     300
```

```
GCCCAAGGGA ATTTAAAATT TGATATTTAT GATGAAGATA ATATAAGTTC TAAGTTAAAT      360

AGTTTAGAAA ATGCAAGACT TTGTCCAAAT AATGAAAAGG GAAACATATA TAGAGGTAGT      420

TGTCCAGATT ACGGAAAAAC GTTTTCGATG GACTTGGATA AGATGAATA TAGTGAAGAT       480

TTCTTAAATG AAATTAGTTT GGGTTTATTA ATAAGAAGT TGTTGATTGA TGTGGAAATC       540

CCAGTTAATA TGAGTGGGCT AGCTATGTAC CAAGGTTTGT TTGCAAATTG TCCTTATGAC      600

AAAAATCATG TTAATGATAT AAAAAATGAA AAAGAGTATG ATATGTGTTT TGATAAATTC      660

TATAGCAATA AACAGGATAT ATCTACAAGG ATTAAAAAAT ACCCGTTAAT AAGTAAATAT      720

ACATATTTTG GGTCACATGG GTTAGGGGGG AGATTAGGTT CTAATACCGA ATATCCTTTA     780

CACATTTATA ACCCAATTGA AAATTATAGA ACACAAAAAA TGAGATATCC TAAATTAGTC      840

GAAACTTTGG AAGATTGTTC GATATATTCT CATTGTATCG GACCCTGTTT TGATAGAGAT     900

TTTGATAACA AATGCTTTCG CGATTTACCT GTAGCTTTTA ATCACAAAAC AAAAGAATGT     960

ATAATAATAG GAACTCATGA AGAAAAAAAA ACAACAAATT GCAACTCAGA CAATTCGAGA    1020

AATAATGGTA GATGTTTTTC ATCTATAAAA AAAGAAAAGG GAAAGGATTG ACATATGCA      1080

TCTTCTTTTT TGCGTCCAGA TTATGAAACA AAGTGCCCAC CAAGATACCC ACTAAATAAT    1140

AGTGAATTTG GTTACTTTAA TTATAACACT GGAAACTGCG AATCACCTAC AAAATTATAC    1200

GATAATAGTG TAATTAGCTT TAATGAATGT ATTGAGAAAT TGTTTAACTT TAATTATGCG    1260

AATGAGGACC CTGAGGAAAA AAGGAATAAT TATTTATGGG GAGTTTGGGT TTTAGGAAAT    1320

AAACAAAATA AACTAAATTC AATGAATGAT TTGGGAGTGT GTGCATTATT AAAAGAAAAA    1380

CCAACATGTG TTTTAAAAAA ACAAAATTAT TACTCCTTTA CTAATTTAAC AGCAAATTAT    1440

TTTGATAATA ATCAAAATAT TGAGTATCCA GATATCGAAA ATGTCAAAAT ATGGAAAAAT    1500

AGAAATTCTG AATTGAGTGA TAATCTAAAA TATAATGATA AAAAGTTTAA AAATTCCGAT    1560

ATAAATAAAG GAATGGCAAT AAATATGAAT GATATTAATG AAATAAAAGA AAATAGTAAA    1620

CTCCAAACTA ATAAGGGCAA CGAAACGAAA AAGACAAAAT ATGGATTATA CAATTATCCG    1680

ATTACACCAA TATCATATCT TCAAATACAT CATAAAATGG AATTAAAAAA TTATAATATG    1740

GATTCTGAAA ATTCTTTCAC ATCTTTCCAT AATAGAATGC TCCAACTCAC TATGAAGGGA    1800

ATAGTAAATT TAGCACCGGC GTAAATAACA AAAGAGAGAA TACATATGGA ACTCAGGATA    1860

TAAATTTAAA TAGAAATAAT AATTATAATC AACCAAAAAA TAAACCTAAT CCCAAGCCGA    1920

ATATAGATAG GTTTGATATT GAAAAAAATC ATATATATAT TGATTGGAAA CAAGATGGTA    1980

AATATGGAAG CGGTAAATTA AAATATAATA TAATATCACA TGAAACCGCT GATACTATTC    2040

AATCATTATT AATTACCGAC AAAGATGACA TATGTCCTAA TCATTATTCT CCTGGAAGAG    2100

CGCAAGGAAG TTGCCCTAAT TATGGTAAAT CGATTGTTGT TAAAACACCT GAAAGTATTA    2160

ATGGTAATGA ACATTTGAAT TCAAATTTTT TAAATGAAAT ACGTACTGGG TACCTTAACA    2220

AATATATGAA ATCTAATGTT GAACTTCCAT ATGAAAAAAG TGGGTTAGCT ATGCATCATG    2280

GTGATTTAAG TGTATGCCCC AAATCTTGGG ATGAAGAAAA TTTGTATAAA AAAAATAGAG    2340

ATTATAATTA TGATATGTGC AAAAGCACTG TAATGAAATC GACTATACCA TTGAAAATGT    2400

TTGATTATAA AACTAAAAAA CTGTTATATT TTGGTCTTTA TGGTTTAGGG GGGCGATTGG    2460

GATCTAATAT TTCAAAAGTA AAAAATATAT TTAAATCACA GCCAAATAAC ATAACATTAC    2520

CAATGTTTAA TCCATCATCA ATAAAAAATT TACTTGATTG TTCATTATAT AGTTATTGTT    2580

TAGGTCCATG CCTGGAAAAT GCATATAATA ATAAATGTTT CCGTAGTCTG CCTGCATATT    2640
```

```
TTAATCATGA AACAAATGAA TGTATAATAT TAGGAACACA CGAACAAGAA AGGAATAATA    2700

ATTGTAGAAC GAGGAGATCT GATACAGATA AACCGAATTG CCAGAATGTT AGAAAAAATA    2760

TATCAACAAA AAATTGGACA TATGTAACAT CATTTATTAG GCCAGACTAT GAAGAGAAAT    2820

GCCCACCAAG ATATCCTCTC AAATTTAAAA GTTTTGGAAA ATATGATGAA GAAACAGGAA    2880

AATGCAAAAG TCTTATAAAT AAAAAGAATA TCATTAATAT TCCTTTGTTT TCTTCTTGTT    2940

TAGAATATAT GTTCATAATG TATCCTTCTG TTTTACAGAG AACTGAAAAA AAAAATTATT    3000

GGGGTGTGTG GGTTGCAAGT GAATCTGTTA ATTCGAGTAA TTTGTATAAT GCTAAAGGAG    3060

AATGTTATTA TATAAATGAA AAACCTAATT GTGTTATTGA CAAAGTAAAT CATTTCTCAT    3120

TTACTTCCCT CACAACAAAT GATATTGATT TTAATCAAAA TATTAATCTC GTAAAACTTG    3180

ATGAATTAGT CATAAATAAT GACCAATCAT CTTCACATAA TAGAGCAAAA TATAATACGC    3240

CTATTGAAAA TTCTGAATCT ACTATTGTAA GAAAACATAA TATTCTGAAC ATTTTCGTAG    3300

TTTAAAAATT AACAGTTATA CACCAAATAG GAGGGGAGAA AATTTTGCAA AGGAAAGTGA    3360

TTCTACAAGA AATACCGATG AATCGAAAAT GGATGAGGTG ATAAGGAAAC GTGAAGAAGC    3420

TGCAAAGAAT GCTGAGATAA TAAGAAAATT TGAAGAAGCA CAAAAGGCTG CGTGGGCAAA    3480

AAAAGCAGAA GAGGAAAGGA AAAAGGCTGA AGCTGTAAAA AAAGCAGAGG AGGAAAGAAA    3540

ACGAATTGAA GCTGAAAAGA AGCAGAGGA GGAAAGAAAA CGAATTGAAG CTGAAAAGAA    3600

AGCAGAAGAA GAAAGAAAAC GAATTGAAGC TGAAAAGAAA GCAGAAGAGG AAAGAAAAT    3660

AATTGAAGCT GCAAAGAAAG CAGAAGAAGA AAGAAAACGA ATTGAAGAAG CTAAAAAAGC    3720

AGAAGAGGAA AGAAAAAAAA TTGAGGCTGC AAAGAAAGCA GAAGAGGAAA GAAAAAAGGC    3780

TGAAGCTGTA AAAAAAGCAG AAGAGGCAAA AAAAAAGGCT GAAGCTGCAA AGAAAGCATT    3840

GAAGCTGAAA GAAAGCAGAA GAGGAAAGAA AACGATTGAA GCTGTAAAAA AGCAGAAGA    3900

AGAAAGAAAA CGAATTGAAG CTGAAAAGAA AGCAGAAGAG GAAAGAAAAC GAATTGAAGC    3960

TGTAAAAAAG CAGAAGAAGA AAGAAAACGT TGAAGCTGAA AAGAAAGCAG AAGAGGAAAG    4020

AAAAATAATT GAAGCTGCAA AGAAAGCAGA AGAAGAACGA ATAAAGCGTG AAGCTGTAAA    4080

GAAAGAAGAA GAAGAAGTAA TAAAAAAAAA CAGCAATCTT TCTGAAAAAA AACAGCAAT    4140

CTTTCTGAAA AAAATTCGA ATAATTATGA AACCGCAATA TTGATGATAA TAGTTTTAAA    4200

AAATTAGATG AAGAAGAGTA TAAATCAAGA AATATTGATA ATACACGGAA TAAAATCATA    4260

AGCATGTCAA AGGAAAATAT GTGTACTAAC GATGTTTCAT CAAAATATTG TGACTATATG    4320

AAAGACAAAA TATCATCTGG AAATTGTTCG AATGATGAAA GGAAACAATT ATGCTGCTCA    4380

ATATCAGATT ATTGCTTAAA CTACTTTGAT TATAATTCAA ATAAATATTA TGATTGTACA    4440

AAGAAGGAAT TTTCAGATCC TTTATATAAA TGCTTTAGTA ACGAGGAATA TTCAAGTATG    4500

TAAAAATCAT AAATAAAGAA TTGTATATTA CATATCAAAC TAATTCCATA TTAAAATGCT    4560

ATAATATGTT TTAAGTTACG TTTTTTTATA GAAGCGGTTT ATTTTGCTGG GGCGGGAATA    4620

ATAATGTCAA TCCTGATTGC CATATGTTTA AAAATTATAG GAAAAAAATG GTATGAAGAA    4680

ATGCCACAAA AAATTATATA TGTATTATGT TTATCTCTCT TAAATTTTTC AAATAAATTT    4740

TTTAATAATA ATATAAGTTC CTAGTCCTGC AGTAGTTTTA AAACATTCAT TATTATTTTT    4800

ATAGGTTTAA GGAAGTTGCT TTTGATGAAA TTGTTGAAGA TTATGATAAA GTCTATACGT    4860

TAGCTATGAT ATGTAATAAT ATTTCAAAAA ATTATTTAAT AATTTGTTAG TTTTTTATAC    4920

TTAAAATTTG TTCAATTAAA TGTTACGCAT TGAAAAATAC ATCTGCATAT ATATTTTTAT    4980

TTTCATGTCT TTTTAGCTAG CGAAAAATTA TAGGAACCGG TCCTATTAT ATTACCCAAT    5040
```

```
TAGACAGATG AAAAAGGCGT ATTATATATT TTAGAATAAT AAATATATAC ATACGGAAAT      5100

TTATACAGCA CAATATATAT GTATACAAAC GTATATATTT ATGTGTATTC AAATAAATAT      5160

ACATATTCTA AAAGAATTAT AAAATATTAT GCAATTTTCA ATAAATATA AAATTTTGTA      5220

TTATTAATAA TATAATTATG TGTTAATTTG TGATGTTTTA TATTTAGCAT AATTGCTATA      5280

ATTATTTTTT ATTCTGTTAA TTTTTTGAGT TTTAATGTAC TCAATAACTT AGTGCTTTAG      5340

TTATACTGAA AACCATAAAT ATTTTATAAT TTAGATAAAT GTTCATTATA GAAGGGAAAA      5400

TATTAATGGA AAATATGCAA CGATAGAAAA CTG                                  5433

(2) INFORMATION FOR SEQ ID NO:2:

(i) SEQUENCE CHARACTERISTICS:
        (A) LENGTH: 3126 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmodium berghei (xi) SEQUENCE DESCRIPTION: SEQ ID NO:2:

AAATAACTAT ATTTGAAAGT ATTTTTTGAG GGATGTTTGT AAAATGAATT GTTAAAATAA        60

TTGTTGTTTT AGTATTATTT GGAGTATGCC GATGCTTTTA ATTTAATTTT TTTGCGGGTA       120

ATGGTTAATT GAATTTACTT GTAGATATAT ACTATATGCA TATATAAATT TTTTCAATTA       180

CTGCAATAAT ATAAAGTATG AAAGTATATT GCAACATTTT TGGATTCTGC TTTTTTATAT       240

CCTTATGGAT TCCTTCTATA CGGGGCATAG ATAACCCACA AGAAGATTTT ATGGACAGAT       300

TTGATATCCT AAACAACCAT GTAAACATAA AATGGACGAA CTCTGGATCA CTAGGAAAAG       360

GGGATTTCAA ATTTGATATT TGTAAGATAA AAAAGGAATT AGCATCAAAA AAAATTATTT       420

CATTTTTATG TAAATTATCA ATAAATTTGT TTTTTTTTGA CACTTGAATT ATCCTGTAAT       480

ATTATTTTCA TGCATTTACG TTATATTAGA TGATGAAGAT AATATAAATT CTAAGTTTAA       540

TACTTTAGAA AGTGCACAAC TTTGTTCAAA TCATGAAAAT GATGGGATAT ATAGAGGTAG       600

TTGCCCAGAT TACGGAAAAA CATTTTCGAT GAACTTGGAT AAAGATGAAT ATAATGAAGA       660

TTTCTTAAAT GAAATTAGTT TGGGCTTATT AAATAAGAAG TTGTTGATTG ATTTGGAAAT       720

CCCAGTTAAT ATGAGTGGGC TAGCTATGTA CCAAGGTTTG TTTGCAAATT GTCCTTATGA       780

CAAAAATCAT GCTAATGATA TAAAAAATGA AAAAGAGTAT GATATGTGTT TTGATAAATT       840

CTATAGAAAT AAACAGAATA TATCTACAAG AATTAAAAAA CAGCTGTTAA TAAGTAAATA       900

TACATATTTT GGATCACATG GGTTAGGGGG TAGATTAGGT TCTAATACCG AATATCCTTT       960

ACACATTTAT AATCCAATTG AAAATTATAA AACAAAACAA ATGAGATATC CTAAATTAGT      1020

CGAAACTTTG GAAGACTGTT CGATATATTC TCATTGTATC GGGCCATGTT TTGATAGAGA      1080

TTTTGATAAC AAATGCTTTC GCGATTTACC TGTAGCTTTT AATCACAAAA CAAAGGAATG      1140

TATAATAATA GGAACTCATG AAGAAAAAAA AACAAAAAAT TGCAACTCAG ACCATTCGAG      1200

AAATAATGGT AGATGTTTTT CATCTATAAA AAAAGAAAAG GGAAAAGATT GGACATATGT      1260

ATCTTCTTTT TTGCGTCCAG ATTATGAAAC AAAGTGCCCA CCAAGATACC CACTAAATAA      1320
```

```
TAGTGAATTT GGTTACTTTA ATTATAATAC CGGAAAATGT GAATCACCTA CAAAGTTATA      1380

CGATAATACC GTAATTAGCT TTAATCAATG TATTGAGAAA TTGTTTAGCT TTAATTATGC      1440

GAATGAAAAT CCAGATCAAA AAAGGAGTAA TTATTTATGG GGAGTTTGGG TTTTAGAAAA      1500

TAAACAAAAT AAACTAAATT CAATGAATGA TTTGGGTGTG TGTGTATTAT TAAAAGAAAG      1560

GCCAACATGT GTTTTAAAAA AACAAAATTA TTACTCCTTT ACTAATTTAA CAGCAAACTA      1620

TTTTGATAAT AATCAAAATA TTGAGTATCC AGATATCGAA AATGTCAAAA TAGGGAAAAA      1680

TCGAAATTCT GAATTGAGTG GAAATCTAAC ATATAATGAT AAAAAGTTTA AAATTCCAA       1740

TATAAATAAA GGAATGGTAA TAAGTATGAA TGATATTAGT GAAATAAAAG AAAATAGTAA      1800

ACTCCAAACT AATAAACGCA ACGAAGGAAA AAAGACAAAA TATGGATTAT ATAATTATCC      1860

GATTACCCCA ATATCATATC TTCAAATAAA TCATAAAAGG GAATTAACAA AAAAATATAT     1920

GTATTTTGAA AATTCTTTAA CCCCTTCTCA TAATACGGGT GCTTCAATCC GTTATGAAGG      1980

GAATAATAGA CTTGGCATTG ACGCAAATAA CAACAGGAGG AATACATATG GAACTCAGGA      2040

TATAAATTTA AAAAGAATAA TAATTATAAA CAACCAAAAA ATAAACTTAA TCCTCAAGCC      2100

GAATATATGG ATAGGTTTGA TATTGAAAAA AATCATATAT ATATTGATTG GAAACAAGAT     2160

GGTAAATATG GAAGCGATAA ATTAAAATAT AATATAATAT CACATGAAAC CGCTAATACT     2220

GTTCAATCAT TATTAATTAC CGACAAAAAT GACATATGCC CTAACCATTA TTCTCCTGGA     2280

AGAGCACAAG GAAGTTGTCC TAATTATGGT AAATCGATTA TTGTTAAAGC ACTTGAAGGT     2340

ACTAATGGAG ATGAATATTT TAATTTAAAT TTTTTAAATG AAATACGTAC TGGGTACCTT     2400

AACAGATATA TGAAATATGA TGTTGAACTT CCATATGAGA AAAGTGGATT AGCTATGCAT     2460

CATGGTGATT TAAATGAATG CCCCAAATCT TTGGATGAAG AAAATTTGTA TAAAATAAAA     2520

AGTGATTATA ATTATGGTAT GTGCAAAAGT ACTGTACTTA AATCGAATGT ACCATTTAAA     2580

ACGTATAATT ATAGAACTAA AAAACTGTTA TATTTTGGTC TTTATGGTTT AGGGGGGCGA     2640

TTGGGATCTA ATATGTCAAA AATAAAAAAT ATATTTAAAT CACGCCCAAA TAACATAACA     2700

TTACCAATGT TTAATCCATC ATTAATAAAA AATTTACTTG ATTGCTCATT ATATAGTTAT     2760

TGTTTAGGTC CGTGCCTGGA AAATGCATAT AATAATAAAT GTTTCCGTAA TTTGCCAGCA     2820

TATTTTAATC ATGAAACAAA AGAATGTGTA ATATTAGGAA CACACGAACA AGAAAGAGTT     2880

AATGATTGTA GAAAGAGGAA AGAGGATATA AATAAACCTA ATTGCCAAGA TGTTAGAAAA     2940

ACTCCATTAT CAAAAGATTG GACATATGTC ACTTCATTTA TTAGACCAGA CTATGAAGAG     3000

AAATGCCCAC CAAGATATCC TCTCAAATTT AAAAGTTTTG GAAAATATGA TGAAGCAACA     3060

GGAAAATGCA AAAGTCTTAT AAATAAAGAG TATATCATTG ATATTCCTTG GTTTTCTTCT     3120

TGTTTA                                                                3126

(2) INFORMATION FOR SEQ ID NO:3:

(i) SEQUENCE CHARACTERISTICS:
        (A) LENGTH: 1194 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Plamodium berghei
```

(xi) SEQUENCE DESCRIPTION: SEQ ID NO:3:

```
AGAAACAAAT TGAAGCTGCA AAGAAAGTAG AAGAAGAAAG AAAAAGAATT GAAGAAGCTA        60

AGAAATCAGA AGAAGAAAGA AAAAGAATTG AAGAAGCTAA GAAAGCAGAA GAAGAAAGAA       120

AAAGAATTGA AGCTGCAAAG AAAGCAGAAG AAGAAAGAAA AAGAATTGAA GAAGCTAAGA       180

AAGCAGAAGA GGAAATAAAA AAAGACAGCA ATCTTGCTGA AAAAAAAATT TCGAGTAGTA       240

ATTATGAAAC GCGCCATATT GATGATAATA GTTTTAAAAA ATTAGATGAA GCAGAGTATA       300

AATCAAGAAA TATTGATAGT ACACGGAATA AAATCATAAG CATGTCAAAG GAAAATATGT       360

GTATTAACGA CATTTCATCA AAATATTGTG ACTATATGAA AGACAAAATA TCATCTGGAA       420

GTTGTTCGAA TGATGAAAGG AAACAATTAT GCTGCTCAAT ATCAGATTAT TGCTTAAACT       480

ATTTTGATTA TAATTCAAAT AAATATTATG ATTGTACAAA GAGGGAATTT TCAGATCCTT       540

TATATAAATG CTTTAGTAAA GAGGAATATT CAAGTATGTA AAAATCATAA ATAAGAATTG       600

CATATTATAC ACAAAAATAA TTCCATATTA AAATGCTATA ATATTTCTTT TAAGTTACGT       660

TTTTTTATAG AAACGGTTTA TTTTGCTGGG GCGGGAATAA TAATGTCCAT CCTGATTGCC       720

ATATGTTTAA AACTTATAGG AGGAAGATGG TACGAAGAAA CATCACAAAA ATTATATGTA       780

TTATGTTTAT CTCTTTTAAA ATTTTCAAAT AAATTTTTTA ATAATAATAA CAGTTGCTAG       840

TTCTGTATAT TTTAAAACAC CCATTATTAT TTTTATAGGT TTAAGGAAGT TGCTTTTGAT       900

GAAATTGTTG AAGATTATGA TAAAGTCTAT ACGTTAGCTA TGATATGTAA TAATATTTCA       960

AAAAATAATT TAATAATTTG TTATTTTTTT ATATTTAAAA TTTATTCAAT TAAATACTAC      1020

GTATTGAAAA ATATACGTAT ATATATATAT TTTTATTTTC ATGCCTTTTT AGCTAACGAA      1080

CAAATATAGG AATCGCCCCA ATTATATTAC CCAATTAGAC AGATAAAAAA GGCATATTGT      1140

ATATTTTAAA ATAATAAATA TATACATACA CAAGTTTATA CAACACAAAA TATG           1194
```

(2) INFORMATION FOR SEQ ID NO:4:

(i) SEQUENCE CHARACTERISTICS:
  (A) LENGTH: 1362 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Plasmodium falciparum (xi) SEQUENCE DESCRIPTION: SEQ ID NO:4:

```
CCAAATAATC ATATATTCAT AGAATGGCAA AAGGAAGGTG AATATGGAAA TGACGAATTT        60

AAATATAATA TTATATCAAA TAAAACAGCA GGTACAAGTC AATCATTATT CCATAATTAT       120

AAAGACAAAA CATGTCCAAA TCATGTTTAT GAAGGGAGGG CACATGGTAG TTGTCCAAAT       180

TATGGTAAAG CTATTATTGT ACAAAATCTT CTAGGTGAAG AATATGATAA GAATTTTAAT       240

TTGAATTTTT TAAATGAAAT ACGTACAGGA TACCTTAACA AATATTTTAA GAAGGATGTC       300

GAAATATCTT ATGAAAATAG TGGAATAGCT ATGCATAATA ACATGTTAAG AAGTTGTCCG       360

GTTCATGAAA ATGAAGAAAA ATTATTTTCT GTGAAAACGG ATTATAATTA TAAAATGTGT       420

AAATCTAAAA TATTTTCAAA TCGTTTTACC ATGAAGGAGT ATGACCCCAA AACACGATTG       480
```

```
TTTATGTATT ATGGTTTGTA TGGTTTAGGT GGAAGATTAG GTGCTAATAT TAAACGAGAT      540

AAACAGAAAG AAAAAAAATA TGAAGATAAT ATAACATTAC CAATGAAAAA TCCATCACTA      600

ATTAAGAATT TGTTCGACTG CTCTATATAT TCTTATTGTT TGGGTCCTTG TTTAGAAAAT      660

TCTTTTGGTA ATAAATGTTT CCGTAATCTG CCTGCTTATT ATAATCATTT AACAAATGAA      720

TGTGTTATAT TGGGTACACA CGAACAAGAA AGAACAAATT CGTGTAGAAG AACGAAAGAA      780

GAAAAGAAAA AACCTAATTG TCAGATATTA AGAAAAACAA CTGATTCGAA AGATTGGACA      840

TATGTCTCTT CATTTATCAG ACCTGATTAT GAAACAAAAT GTCCACCTAG ATACCCTTTA      900

AAATCAAAAG TTTTTGGAAC CTTTGACCAA AAAACAGGAA AATGTAAAAG TCTCATGGAC      960

AAAGCATATG AAGTTGGAAT TAATAAATTT TCAGTCTGTT TAGAATATTT ATTTTTAGTA     1020

TCACCTAAGG ATTTATATAA TAGCGGAAGA AATAACTATT GGGGTATTTG GGCAGCAGAT     1080

CATTCTGTTA ATGAAAATAA TATTGAAATA GCAAATGGTA AATGTTATCA TTTAGTTGTA     1140

AAACCAACAT GTGTCATAGA TAAGGAAAAC CATTTTTCTT TTACAGCGCT TACAGCAAAT     1200

ACTGTTGATT TTAACCAATC CGTTAATATA AGAAAGATTG AAGAATTAAC TGAATATGGA     1260

AACAATTATG CTGCTCAATA TCAGATTATT GGATCCTTAA GCCGAATTCC AGCACACTGG     1320

CGGCCGTTAC TAGTGGATCC GAGCTCGGTA CCAAGCTTGG CG                       1362

(2) INFORMATION FOR SEQ ID NO:5:

(i) SEQUENCE CHARACTERISTICS:
        (A) LENGTH: 1507 amino acids
        (B) TYPE: amino acid
        (C) STRANDEDNESS:
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Plasmodium yoelii (xi) SEQUENCE DESCRIPTION: SEQ ID NO:5:

Met Lys Ile Tyr His Asn Ile Phe Gly Phe Cys Ile Phe Ile Ser Leu
1               5                   10                  15

Trp Thr Pro Ser Ile Arg Ala Ile Asp Asn Pro Gln Glu Asp Phe Met
            20                  25                  30

Asp Arg Phe Asp Ile Leu Asn Asn His Val Asn Ile Lys Trp Thr Asn
        35                  40                  45

Ser Gly Ser Leu Ala Gln Gly Asn Leu Lys Phe Asp Ile Tyr Asp Glu
    50                  55                  60

Asp Asn Ile Ser Ser Lys Leu Asn Ser Leu Glu Asn Ala Arg Leu Cys
65                  70                  75                  80

Pro Asn Glu Lys Gly Asn Ile Tyr Arg Gly Ser Cys Pro Asp Tyr
                85                  90                  95

Gly Lys Thr Phe Ser Met Asp Leu Asp Lys Asp Glu Tyr Ser Glu Asp
            100                 105                 110

Phe Leu Asn Glu Ile Ser Leu Gly Leu Leu Asn Lys Lys Leu Leu Ile
        115                 120                 125

Asp Val Glu Ile Pro Val Asn Met Ser Gly Leu Ala Met Tyr Gln Gly
    130                 135                 140

Leu Phe Ala Asn Cys Pro Tyr Asp Lys Asn His Val Asn Asp Ile Lys
145                 150                 155                 160
```

-continued

```
Asn Glu Lys Glu Tyr Asp Met Cys Phe Asp Lys Phe Tyr Ser Asn Lys
            165                 170                 175
Gln Asp Ile Ser Thr Arg Ile Lys Lys Tyr Pro Leu Ile Ser Lys Tyr
            180                 185                 190
Thr Tyr Phe Gly Ser His Gly Leu Gly Gly Arg Leu Gly Ser Asn Thr
            195                 200                 205
Glu Tyr Pro Leu His Ile Tyr Asn Pro Ile Glu Asn Tyr Arg Thr Gln
            210                 215                 220
Lys Met Arg Tyr Pro Lys Leu Val Glu Thr Leu Glu Asp Cys Ser Ile
225                 230                 235                 240
Tyr Ser His Cys Ile Gly Pro Cys Phe Asp Arg Asp Phe Asp Asn Lys
            245                 250                 255
Cys Phe Arg Asp Leu Pro Val Ala Phe Asn His Lys Thr Lys Glu Cys
            260                 265                 270
Ile Ile Ile Gly Thr His Glu Lys Lys Thr Thr Asn Cys Asn Ser
            275                 280                 285
Asp Asn Ser Arg Asn Asn Gly Arg Cys Phe Ser Ser Ile Lys Lys Glu
            290                 295                 300
Lys Gly Lys Asp Trp Thr Tyr Ala Ser Ser Phe Leu Arg Pro Asp Tyr
305                 310                 315                 320
Glu Thr Lys Cys Pro Pro Arg Tyr Pro Leu Asn Asn Ser Glu Phe Gly
            325                 330                 335
Tyr Phe Asn Tyr Asn Thr Gly Asn Cys Glu Ser Pro Thr Lys Leu Tyr
            340                 345                 350
Asp Asn Ser Val Ile Ser Phe Asn Glu Cys Ile Glu Lys Leu Phe Asn
            355                 360                 365
Phe Asn Tyr Ala Asn Glu Asp Pro Glu Glu Lys Arg Asn Asn Tyr Leu
            370                 375                 380
Trp Gly Val Trp Val Leu Gly Asn Lys Gln Asn Lys Leu Asn Ser Met
385                 390                 395                 400
Asn Asp Leu Gly Val Cys Ala Leu Leu Lys Glu Lys Pro Thr Cys Val
            405                 410                 415
Leu Lys Lys Gln Asn Tyr Tyr Ser Phe Thr Asn Leu Thr Ala Asn Tyr
            420                 425                 430
Phe Asp Asn Asn Gln Asn Ile Glu Tyr Pro Asp Ile Glu Asn Val Lys
            435                 440                 445
Ile Trp Lys Asn Arg Asn Ser Glu Leu Ser Asp Asn Leu Lys Tyr Asn
            450                 455                 460
Asp Lys Lys Phe Lys Asn Ser Asp Ile Asn Lys Gly Met Ala Ile Asn
465                 470                 475                 480
Met Asn Asp Ile Asn Glu Ile Lys Glu Asn Ser Lys Leu Gln Thr Asn
            485                 490                 495
Lys Gly Asn Glu Thr Lys Lys Thr Lys Tyr Gly Leu Tyr Asn Tyr Pro
            500                 505                 510
Ile Thr Pro Ile Ser Tyr Leu Gln Ile His His Lys Met Glu Leu Lys
            515                 520                 525
Asn Tyr Asn Met Asp Ser Glu Asn Ser Phe Thr Ser Phe His Asn Thr
            530                 535                 540
Asn Ala Pro Thr His Tyr Glu Gly Asn Ser Lys Phe Ser Thr Gly Val
545                 550                 555                 560
Asn Asn Lys Arg Glu Asn Thr Tyr Gly Thr Gln Asp Ile Asn Leu Asn
            565                 570                 575
```

-continued

```
Arg Asn Asn Asn Tyr Asn Gln Pro Lys Asn Lys Pro Asn Pro Gln Ala
            580                 585                 590
Glu Tyr Met Asp Arg Phe Asp Ile Glu Lys Asn His Ile Tyr Ile Asp
        595                 600                 605
Trp Lys Gln Asp Gly Lys Tyr Gly Ser Gly Lys Leu Lys Tyr Asn Ile
    610                 615                 620
Ile Ser His Glu Thr Ala Asp Thr Ile Gln Ser Leu Leu Ile Thr Asp
625                 630                 635                 640
Lys Asp Asp Ile Cys Pro Asn His Tyr Ser Pro Gly Arg Ala Gln Gly
                645                 650                 655
Ser Cys Pro Asn Tyr Gly Lys Ser Ile Val Lys Thr Pro Glu Ser
                660                 665                 670
Ile Asn Gly Asn Glu His Leu Asn Ser Asn Phe Leu Asn Glu Ile Arg
            675                 680                 685
Thr Gly Tyr Leu Asn Lys Tyr Met Lys Ser Asn Val Glu Leu Pro Tyr
        690                 695                 700
Glu Lys Ser Gly Leu Ala Met His His Gly Asp Leu Ser Val Cys Pro
705                 710                 715                 720
Lys Ser Trp Asp Glu Glu Asn Leu Tyr Lys Lys Asn Arg Asp Tyr Asn
                725                 730                 735
Tyr Asp Met Cys Lys Ser Thr Val Met Lys Ser Thr Ile Pro Leu Lys
                740                 745                 750
Met Phe Asp Tyr Lys Thr Lys Lys Leu Leu Tyr Phe Gly Leu Tyr Gly
            755                 760                 765
Leu Gly Gly Arg Leu Gly Ser Asn Ile Ser Lys Val Lys Asn Ile Phe
        770                 775                 780
Lys Ser Gln Pro Asn Asn Ile Thr Leu Pro Met Phe Asn Pro Ser Ser
785                 790                 795                 800
Ile Lys Asn Leu Leu Asp Cys Ser Leu Tyr Ser Tyr Cys Leu Gly Pro
                805                 810                 815
Cys Leu Glu Asn Ala Tyr Asn Asn Lys Cys Phe Arg Ser Leu Pro Ala
                820                 825                 830
Tyr Phe Asn His Glu Thr Asn Glu Cys Ile Ile Leu Gly Thr His Glu
            835                 840                 845
Gln Glu Arg Asn Asn Cys Arg Thr Arg Arg Ser Asp Thr Asp Lys
        850                 855                 860
Pro Asn Cys Gln Asn Val Arg Lys Asn Ile Ser Thr Lys Asn Trp Thr
865                 870                 875                 880
Tyr Val Thr Ser Phe Ile Arg Pro Asp Tyr Glu Glu Lys Cys Pro Pro
                885                 890                 895
Arg Tyr Pro Leu Lys Phe Lys Ser Phe Gly Lys Tyr Asp Glu Glu Thr
            900                 905                 910
Gly Lys Cys Lys Ser Leu Ile Asn Lys Lys Asn Ile Ile Asn Ile Pro
        915                 920                 925
Leu Phe Ser Ser Cys Leu Glu Tyr Met Phe Ile Met Tyr Pro Ser Val
    930                 935                 940
Leu Gln Arg Thr Glu Lys Lys Asn Tyr Trp Gly Val Trp Ala Ser
945                 950                 955                 960
Glu Ser Val Asn Ser Ser Asn Leu Tyr Asn Ala Lys Gly Glu Cys Tyr
                965                 970                 975
Tyr Ile Asn Glu Lys Pro Asn Cys Val Ile Asp Lys Val Asn His Phe
            980                 985                 990
Ser Phe Thr Ser Leu Thr Thr Asn Asp Ile Asp Phe Asn Gln Asn Ile
```

-continued

```
               995                 1000                1005
Asn Leu Val Lys Leu Asp Glu Leu Val Ile Asn Asn Asp Gln Ser Ser
    1010                1015                1020

Ser His Asn Arg Ala Lys Tyr Asn Thr Pro Ile Glu Asn Ser Glu Ser
1025                1030                1035                1040

Thr Ile Val Arg Lys His Asn Ser Ala Pro Glu His Phe Arg Ser Leu
                1045                1050                1055

Lys Ile Asn Ser Tyr Thr Pro Asn Arg Arg Gly Glu Asn Phe Ala Lys
            1060                1065                1070

Glu Ser Asp Ser Thr Arg Asn Thr Asp Glu Ser Lys Met Asp Glu Val
        1075                1080                1085

Ile Arg Lys Arg Glu Glu Ala Ala Lys Asn Ala Glu Ile Ile Arg Lys
    1090                1095                1100

Phe Glu Glu Ala Gln Lys Ala Ala Trp Ala Lys Lys Ala Glu Glu Glu
1105                1110                1115                1120

Arg Lys Lys Ala Glu Ala Val Lys Lys Ala Glu Glu Arg Lys Arg
                1125                1130                1135

Ile Glu Ala Glu Lys Lys Ala Glu Glu Arg Lys Arg Ile Glu Ala
            1140                1145                1150

Glu Lys Lys Ala Glu Glu Arg Lys Arg Ile Glu Ala Glu Lys Lys
        1155                1160                1165

Ala Glu Glu Arg Lys Ile Ile Glu Ala Ala Lys Lys Ala Glu Glu
    1170                1175                1180

Glu Arg Lys Arg Ile Glu Glu Ala Lys Lys Ala Glu Glu Arg Lys
1185                1190                1195                1200

Lys Ile Glu Ala Ala Lys Lys Ala Glu Glu Arg Lys Lys Ala Glu
                1205                1210                1215

Ala Val Lys Lys Ala Glu Glu Ala Lys Lys Lys Ala Glu Ala Ala Lys
    1220                1225                1230

Lys Ala Leu Lys Leu Lys Glu Ser Arg Arg Gly Lys Lys Thr Ile Glu
            1235                1240                1245

Ala Val Lys Lys Ala Glu Glu Glu Arg Lys Arg Ile Glu Ala Glu Lys
        1250                1255                1260

Lys Ala Glu Glu Glu Arg Lys Arg Ile Glu Ala Val Lys Lys Gln Lys
1265                1270                1275                1280

Lys Lys Glu Asn Val Glu Ala Glu Lys Lys Ala Glu Glu Glu Arg Lys
                1285                1290                1295

Ile Ile Glu Ala Ala Lys Lys Ala Glu Glu Arg Ile Lys Arg Glu
            1300                1305                1310

Ala Val Lys Lys Glu Glu Glu Val Ile Lys Lys Asn Ser Asn Leu
        1315                1320                1325

Ser Glu Lys Lys Thr Ala Ile Phe Leu Lys Lys Asn Ser Asn Asn Tyr
    1330                1335                1340

Glu Thr Arg Asn Ile Asp Asp Asn Ser Phe Lys Lys Leu Asp Glu Glu
1345                1350                1355                1360

Glu Tyr Lys Ser Arg Asn Ile Asp Asn Thr Arg Asn Lys Ile Ile Ser
                1365                1370                1375

Met Ser Lys Glu Asn Met Cys Thr Asn Asp Val Ser Ser Lys Tyr Cys
            1380                1385                1390

Asp Tyr Met Lys Asp Lys Ile Ser Ser Gly Asn Cys Ser Asn Asp Glu
        1395                1400                1405

Arg Lys Gln Leu Cys Cys Ser Ile Ser Asp Tyr Cys Leu Asn Tyr Phe
    1410                1415                1420
```

```
Asp Tyr Asn Ser Asn Lys Tyr Asp Cys Thr Lys Lys Glu Phe Ser
1425                1430                1435                1440

Asp Pro Leu Tyr Lys Cys Phe Ser Asn Glu Glu Tyr Ser Lys Ala Val
            1445                1450                1455

Tyr Phe Ala Gly Ala Gly Ile Ile Met Ser Ile Leu Ile Ala Ile Cys
        1460                1465                1470

Leu Lys Ile Ile Gly Lys Lys Trp Phe Lys Glu Val Ala Phe Asp Glu
    1475                1480                1485

Ile Val Glu Asp Tyr Asp Lys Val Tyr Thr Leu Ala Met Ile Ser Ser
    1490                1495                1500

Glu Lys Leu
1505

(2) INFORMATION FOR SEQ ID NO:6:

(i) SEQUENCE CHARACTERISTICS:
        (A) LENGTH: 934 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Plasmodium berghei (xi) SEQUENCE DESCRIPTION: SEQ ID NO:6:

Met Lys Val Tyr Cys Asn Ile Phe Gly Phe Cys Phe Phe Ile Ser Leu
1               5                   10                  15

Asp Trp Ile Pro Ser Ile Arg Gly Ile Asp Asn Pro Gln Glu Asp Phe
            20                  25                  30

Met Arg Phe Asp Ile Leu Asn Asn His Val Asn Ile Lys Trp Thr Asn
        35                  40                  45

Ser Gly Ser Leu Gly Lys Gly Asp Phe Lys Phe Asp Ile Tyr Asp Glu
    50                  55                  60

Asp Asn Ile Asn Ser Lys Phe Asn Thr Leu Glu Ser Ala Gln Leu Cys
65                  70                  75                  80

Ser Asn His Glu Asn Asp Gly Ile Tyr Arg Gly Ser Cys Pro Asp Tyr
                85                  90                  95

Gly Lys Thr Phe Ser Met Asn Leu Asp Lys Asp Glu Tyr Asn Glu Asp
            100                 105                 110

Phe Leu Asn Glu Ile Ser Leu Gly Leu Leu Asn Lys Lys Leu Leu Ile
        115                 120                 125

Asp Leu Glu Ile Pro Val Asn Met Ser Gly Leu Ala Met Tyr Gln Gly
    130                 135                 140

Leu Phe Ala Asn Cys Pro Tyr Asp Lys Asn His Ala Asn Asp Ile Lys
145                 150                 155                 160

Asn Glu Lys Glu Tyr Asp Met Cys Phe Asp Lys Phe Tyr Arg Asn Lys
                165                 170                 175

Gln Asn Ile Ser Thr Arg Ile Lys Lys Gln Leu Leu Ile Ser Lys Tyr
            180                 185                 190

Thr Tyr Phe Gly Ser His Gly Leu Gly Gly Arg Leu Gly Ser Asn Thr
        195                 200                 205
```

```
Glu Tyr Pro Leu His Ile Tyr Asn Pro Ile Glu Asn Tyr Lys Thr Lys
    210                 215                 220

Gln Met Arg Tyr Pro Lys Leu Val Glu Thr Leu Glu Asp Cys Ser Ile
225                 230                 235                 240

Tyr Ser His Cys Ile Gly Pro Cys Phe Asp Arg Asp Phe Asp Asn Lys
                245                 250                 255

Cys Phe Arg Asp Leu Pro Val Ala Phe Asn His Lys Thr Lys Glu Cys
                260                 265                 270

Ile Ile Ile Gly Thr His Glu Glu Lys Thr Lys Asn Cys Asn Ser
                275                 280                 285

Asp His Ser Arg Asn Asn Gly Arg Cys Phe Ser Ser Ile Lys Lys Glu
    290                 295                 300

Lys Gly Lys Asp Trp Thr Tyr Val Ser Ser Phe Leu Arg Pro Asp Tyr
305                 310                 315                 320

Glu Thr Lys Cys Pro Pro Arg Tyr Pro Leu Asn Asn Ser Glu Phe Gly
                325                 330                 335

Tyr Phe Asn Tyr Asn Thr Gly Lys Cys Glu Ser Pro Thr Lys Leu Tyr
                340                 345                 350

Asp Asn Thr Val Ile Ser Phe Asn Gln Cys Ile Glu Lys Leu Phe Ser
    355                 360                 365

Phe Asn Tyr Ala Asn Glu Asn Pro Asp Gln Lys Arg Ser Asn Tyr Leu
    370                 375                 380

Trp Gly Val Trp Val Leu Glu Asn Lys Gln Asn Lys Leu Asn Ser Met
385                 390                 395                 400

Asn Asp Leu Gly Val Cys Val Leu Leu Lys Glu Arg Pro Thr Cys Val
                405                 410                 415

Leu Lys Lys Gln Asn Tyr Tyr Ser Phe Thr Asn Leu Thr Ala Asn Tyr
                420                 425                 430

Phe Asp Asn Asn Gln Asn Ile Glu Tyr Pro Asp Ile Glu Asn Val Lys
                435                 440                 445

Ile Gly Lys Asn Arg Asn Ser Glu Leu Ser Gly Asn Leu Thr Tyr Asn
    450                 455                 460

Asp Lys Lys Phe Lys Asn Ser Asn Ile Asn Lys Gly Met Val Ile Ser
465                 470                 475                 480

Met Asn Asp Ile Ser Glu Ile Lys Glu Asn Ser Lys Leu Gln Thr Asn
                485                 490                 495

Lys Arg Asn Glu Gly Lys Lys Thr Lys Tyr Gly Leu Tyr Asn Tyr Pro
                500                 505                 510

Ile Thr Pro Ile Ser Tyr Leu Gln Ile Asn His Lys Arg Glu Leu Thr
                515                 520                 525

Lys Lys Tyr Met Tyr Phe Glu Asn Ser Leu Thr Pro Ser His Asn Thr
    530                 535                 540

Gly Ala Ser Ile Arg Tyr Glu Gly Asn Asn Arg Leu Gly Ile Asp Ala
545                 550                 555                 560

Asn Asn Asn Arg Arg Asn Thr Tyr Gly Thr Gln Asp Ile Asn Leu Lys
                565                 570                 575

Arg Asn Asn Asn Tyr Lys Gln Pro Lys Asn Lys Leu Asn Pro Gln Ala
                580                 585                 590

Glu Tyr Met Asp Arg Phe Asp Ile Glu Lys Asn His Ile Tyr Ile Asp
    595                 600                 605

Trp Lys Gln Asp Gly Lys Tyr Gly Ser Asp Lys Leu Lys Tyr Asn Ile
610                 615                 620
```

```
Ile Ser His Glu Thr Ala Asn Thr Val Gln Ser Leu Leu Ile Thr Asp
625                 630                 635                 640

Lys Asn Asp Ile Cys Pro Asn His Tyr Ser Pro Gly Arg Ala Gln Gly
                645                 650                 655

Ser Cys Pro Asn Tyr Gly Lys Ser Ile Ile Val Lys Ala Leu Glu Gly
                660                 665                 670

Thr Asn Gly Asp Glu Tyr Phe Asn Leu Asn Phe Leu Asn Glu Ile Arg
                675                 680                 685

Thr Gly Tyr Leu Asn Arg Tyr Met Lys Tyr Asp Val Glu Leu Pro Tyr
690                 695                 700

Glu Lys Ser Gly Leu Ala Met His His Gly Asp Leu Asn Glu Cys Pro
705                 710                 715                 720

Lys Ser Leu Asp Glu Glu Asn Leu Tyr Lys Ile Lys Ser Asp Tyr Asn
                725                 730                 735

Tyr Gly Met Cys Lys Ser Thr Val Leu Lys Ser Asn Val Pro Phe Lys
                740                 745                 750

Thr Tyr Asn Tyr Arg Thr Lys Lys Leu Leu Tyr Phe Gly Leu Tyr Gly
                755                 760                 765

Leu Gly Gly Arg Leu Gly Ser Asn Met Ser Lys Ile Lys Asn Ile Phe
770                 775                 780

Lys Ser Arg Pro Asn Asn Ile Thr Leu Pro Met Phe Asn Pro Ser Leu
785                 790                 795                 800

Ile Lys Asn Leu Leu Asp Cys Ser Leu Tyr Ser Tyr Cys Leu Gly Pro
                805                 810                 815

Cys Leu Glu Asn Ala Tyr Asn Asn Lys Cys Phe Arg Asn Leu Pro Ala
                820                 825                 830

Tyr Phe Asn His Glu Thr Lys Glu Cys Val Ile Leu Gly Thr His Glu
                835                 840                 845

Gln Glu Arg Val Asn Asp Cys Arg Lys Arg Lys Glu Asp Ile Asn Lys
850                 855                 860

Pro Asn Cys Gln Asp Val Arg Lys Thr Pro Leu Ser Lys Asp Trp Thr
865                 870                 875                 880

Tyr Val Thr Ser Phe Ile Arg Pro Asp Tyr Glu Lys Cys Pro Pro
                885                 890                 895

Arg Tyr Pro Leu Lys Phe Lys Ser Phe Gly Lys Tyr Asp Glu Ala Thr
                900                 905                 910

Gly Lys Cys Lys Ser Leu Ile Asn Lys Glu Tyr Ile Ile Asp Ile Pro
                915                 920                 925

Trp Phe Ser Ser Cys Leu
930

(2) INFORMATION FOR SEQ ID NO:7:

(i) SEQUENCE CHARACTERISTICS:
        (A) LENGTH: 242 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:7:
```

-continued

```
Ile Glu Ala Ala Lys Lys Val Glu Glu Arg Lys Arg Ile Glu Glu
1               5                   10                  15

Ala Lys Lys Ser Glu Glu Arg Lys Arg Ile Glu Glu Ala Lys Lys
                20                  25                  30

Ala Glu Glu Glu Arg Lys Arg Ile Glu Ala Lys Lys Ala Glu Glu
                35                  40                  45

Glu Arg Lys Arg Ile Glu Ala Lys Lys Ala Glu Glu Ile Lys
        50                  55                  60

Lys Asp Ser Asn Leu Ala Glu Lys Lys Ile Ser Ser Asn Tyr Glu
65                  70                  75                  80

Thr Arg His Ile Asp Asp Asn Ser Phe Lys Lys Leu Asp Ala Glu
                85                  90                  95

Tyr Lys Ser Arg Asn Ile Asp Ser Thr Arg Asn Lys Ile Ile Ser Met
                100                 105                 110

Ser Lys Glu Asn Met Cys Ile Asn Asp Ile Ser Ser Lys Tyr Cys Asp
                115                 120                 125

Tyr Met Lys Asp Lys Ile Ser Ser Gly Ser Cys Ser Asn Asp Glu Arg
130                 135                 140

Lys Gln Leu Cys Cys Ser Ile Ser Asp Tyr Cys Leu Asn Tyr Phe Asp
145                 150                 155                 160

Tyr Asn Ser Asn Lys Tyr Tyr Asp Cys Thr Lys Arg Glu Phe Ser Asp
                165                 170                 175

Pro Leu Tyr Lys Cys Phe Ser Lys Glu Glu Tyr Ser Lys Thr Val Tyr
                180                 185                 190

Phe Ala Gly Ala Gly Ile Ile Met Ser Ile Leu Ile Ala Ile Cys Leu
                195                 200                 205

Lys Leu Ile Gly Gly Arg Trp Phe Lys Glu Val Ala Phe Asp Glu Ile
210                 215                 220

Val Glu Asp Tyr Asp Lys Val Tyr Thr Leu Ala Met Ile Ser Asn Glu
225                 230                 235                 240

Gln Ile
```

(2) INFORMATION FOR SEQ ID NO:8:

(i) SEQUENCE CHARACTERISTICS:
        (A) LENGTH: 454 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Plasmodium falciparum (xi) SEQUENCE DESCRIPTION: SEQ ID NO:8:

```
Pro Asn Asn His Ile Phe Ile Glu Trp Gln Lys Glu Gly Glu Tyr Gly
1               5                   10                  15

Asn Asp Glu Phe Lys Tyr Asn Ile Ile Ser Asn Lys Thr Ala Gly Thr
                20                  25                  30

Ser Gln Ser Leu Phe His Asn Tyr Lys Asp Lys Thr Cys Pro Asn His
                35                  40                  45

Val Tyr Glu Gly Arg Ala His Gly Ser Cys Pro Asn Tyr Gly Lys Ala
```

-continued

```
        50                  55                  60
Ile Ile Val Gln Asn Leu Leu Gly Glu Glu Tyr Asp Lys Asn Phe Asn
 65                  70                  75                  80

Leu Asn Phe Leu Asn Glu Ile Arg Thr Gly Tyr Leu Asn Lys Tyr Phe
                 85                  90                  95

Lys Lys Asp Val Glu Ile Ser Tyr Glu Asn Ser Gly Ile Ala Met His
                100                 105                 110

Asn Asn Met Leu Arg Ser Cys Pro Val His Glu Asn Glu Glu Lys Leu
                115                 120                 125

Phe Ser Val Lys Thr Asp Tyr Asn Tyr Lys Met Cys Lys Ser Lys Ile
130                 135                 140

Phe Ser Asn Arg Phe Thr Met Lys Glu Tyr Asp Pro Lys Thr Arg Leu
145                 150                 155                 160

Phe Met Tyr Tyr Gly Leu Tyr Gly Leu Gly Gly Arg Leu Gly Ala Asn
                165                 170                 175

Ile Lys Arg Asp Lys Gln Lys Glu Lys Lys Tyr Glu Asp Asn Ile Thr
                180                 185                 190

Leu Pro Met Lys Asn Pro Ser Leu Ile Lys Asn Leu Phe Asp Cys Ser
                195                 200                 205

Ile Tyr Ser Tyr Cys Leu Gly Pro Cys Leu Glu Asn Ser Phe Gly Asn
210                 215                 220

Lys Cys Phe Arg Asn Leu Pro Ala Tyr Tyr Asn His Leu Thr Asn Glu
225                 230                 235                 240

Cys Val Ile Leu Gly Thr His Glu Gln Glu Arg Thr Asn Ser Cys Arg
                245                 250                 255

Arg Thr Lys Glu Glu Lys Lys Lys Pro Asn Cys Gln Ile Leu Arg Lys
                260                 265                 270

Thr Thr Asp Ser Lys Asp Trp Thr Tyr Val Ser Ser Phe Ile Arg Pro
                275                 280                 285

Asp Tyr Glu Thr Lys Cys Pro Pro Arg Tyr Pro Leu Lys Ser Lys Val
290                 295                 300

Phe Gly Thr Phe Asp Gln Lys Thr Gly Lys Cys Lys Ser Leu Met Asp
305                 310                 315                 320

Lys Ala Tyr Glu Val Gly Ile Asn Lys Phe Ser Val Cys Leu Glu Tyr
                325                 330                 335

Leu Phe Leu Val Ser Pro Lys Asp Leu Tyr Asn Ser Gly Arg Asn Asn
                340                 345                 350

Tyr Trp Gly Ile Trp Ala Ala Asp His Ser Val Asn Glu Asn Asn Ile
                355                 360                 365

Glu Ile Ala Asn Gly Lys Cys Tyr His Leu Val Val Lys Pro Thr Cys
370                 375                 380

Val Ile Asp Lys Glu Asn His Phe Ser Phe Thr Ala Leu Thr Ala Asn
385                 390                 395                 400

Thr Val Asp Phe Asn Gln Ser Val Asn Ile Arg Lys Ile Glu Glu Leu
                405                 410                 415

Thr Glu Tyr Gly Asn Asn Tyr Ala Ala Gln Tyr Gln Ile Ile Gly Ser
                420                 425                 430

Leu Ser Arg Ile Pro Ala His Trp Arg Pro Leu Leu Val Asp Pro Ser
                435                 440                 445

Ser Val Pro Ser Leu Ala
                450
```

(2) INFORMATION FOR SEQ ID NO:9:

(i) SEQUENCE CHARACTERISTICS:
        (A) LENGTH: 253 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Plasmodium falciparum (xi) SEQUENCE DESCRIPTION: SEQ ID NO:9:

Arg Gly Ser Cys Pro Asp Tyr Gly Lys Thr Phe Leu Met Gly Phe Glu
1               5                  10                  15

Asp Asn Lys Tyr Ser Glu Glu Phe Leu Asn Glu Ile Ser Phe Gly Phe
            20                  25                  30

Leu Asn Lys Lys Tyr Lys Leu Pro Ile Glu Ile Pro Leu Asn Lys Ser
        35                  40                  45

Gly Leu Ser Met Tyr Gln Gly Leu Phe Lys Arg Cys Pro Tyr Asn Lys
50                  55                  60

Lys His Tyr Ser Met Ile Lys Asn Glu Asn Glu Tyr Asp Met Cys Phe
65                  70                  75                  80

Arg Lys Phe Tyr Asn Asn Ser Asn Ile Ser Thr Arg Ile Tyr Lys Arg
                85                  90                  95

Gly Lys Gln Asn Arg Lys Tyr Ile Tyr Phe Ser Ser His Gly Leu Gly
            100                 105                 110

Gly Arg Leu Gly Ala Asn Ile Glu Glu Pro Leu His Lys Tyr Lys Asn
        115                 120                 125

Asp Glu His Tyr Val Thr Lys Met Arg Tyr Pro Glu Lys Asn Lys Lys
    130                 135                 140

Phe Val Asp Cys Ser Ile Tyr Ser His Cys Ile Gly Pro Cys Leu Tyr
145                 150                 155                 160

Lys Asp Phe Asn Asn Ser Cys Phe Leu Asn Leu Pro Ile Leu Phe Asn
                165                 170                 175

His Gln Thr Lys Glu Cys Val His Gly Thr His Glu Glu Lys Arg Ile
            180                 185                 190

His Asn Cys Gln Ser Gly Ser Thr Asp Gln Asn Ile Gln Arg Cys Phe
        195                 200                 205

Leu Pro Val Lys Lys Glu Lys Gly Asn Gln Trp Thr Tyr Ala Ser Ser
    210                 215                 220

Phe Ile Arg Thr Asp Tyr Met Thr Lys Cys Pro Pro Arg Phe Pro Leu
225                 230                 235                 240

Asn His Thr Met Phe Gly Tyr Phe Asn Tyr Ser Thr Gly
                245                 250

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

Asn Phe Leu Asn Glu Ile Arg Thr Gly Tyr Leu Asn
1               5                  10

(2) INFORMATION FOR SEQ ID NO:11:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

Gly Leu Tyr Gly Leu Gly Gly Thr Leu Gly
1               5                  10

(2) INFORMATION FOR SEQ ID NO:12:

(i) SEQUENCE CHARACTERISTICS:
            (A) LENGTH: 7 amino acids
            (B) TYPE: amino acid
            (C) STRANDEDNESS:
            (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:12:

Gly Leu Gly Gly Arg Leu Gly
1               5

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS:
            (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

Tyr Cys Leu Gly Pro Cys Leu Glu Asn
1               5

(2) INFORMATION FOR SEQ ID NO:14:

(i) SEQUENCE CHARACTERISTICS:
           (A) LENGTH: 9 amino acids
           (B) TYPE: amino acid
           (C) STRANDEDNESS:
           (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:14:

Ile Leu Gly Thr His Glu Gln Glu Arg
1               5

(2) INFORMATION FOR SEQ ID NO:15:

(i) SEQUENCE CHARACTERISTICS:
           (A) LENGTH: 8 amino acids
           (B) TYPE: amino acid
           (C) STRANDEDNESS:
           (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:15:

Lys Cys Pro Pro Arg Tyr Pro Leu
1               5

(2) INFORMATION FOR SEQ ID NO:16:

(i) SEQUENCE CHARACTERISTICS:
           (A) LENGTH: 93 amino acids
           (B) TYPE: amino acid
           (C) STRANDEDNESS:
           (D) TOPOLOGY: linear (ii) MOLECULE TYPE: peptide (iii) HYPOTHETICAL: YES (iv) ANTI-SENSE: NO (xi) SEQUENCE DESCRIPTION: SEQ ID NO:16:

Lys Lys Leu Asp Glu Xaa Glu Tyr Lys Ser Arg Asn Xaa Xaa Xaa Thr
1               5                   10                  15

Arg Xaa Lys Ile Ile Xaa Met Ser Lys Glu Asn Met Cys Xaa Asn Asp
            20                  25                  30

Ile Ser Ser Lys Tyr Cys Asp Tyr Met Lys Asp Xaa Lys Ile Ser Ser
        35                  40                  45

Gly Xaa Cys Ser Xaa Xaa Xaa Arg Lys Gln Leu Cys Cys Ser Ile Ser
    50                  55                  60

Asp Tyr Cys Leu Asn Tyr Phe Asp Tyr Asn Ser Asn Lys Tyr Tyr Asp
65                  70                  75                  80

Cys Thr Lys Xaa Glu Phe Ser Asp Pro Ser Tyr Lys Cys
                85                  90

(2) INFORMATION FOR SEQ ID NO:17:

(i) SEQUENCE CHARACTERISTICS:
           (A) LENGTH: 32 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Oligonucleotide primer for
               P. falciparum EBA175 region"

(iii) HYPOTHETICAL: YES (iv) ANTI-SENSE: NO (xi) SEQUENCE DESCRIPTION: SEQ ID NO:17:

AAATGTGAGA ACGAAATTTC TGTAAAATAT TG                                     32

(2) INFORMATION FOR SEQ ID NO:18:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Oligonucleotide primer for
                the antisence of the P. falciparum EBA175 region"

(iii) HYPOTHETICAL: YES (iv) ANTI-SENSE: YES (xi) SEQUENCE DESCRIPTION: SEQ ID NO:18:

GGATCATCAA ATTCCCTTTT CGTAC                                             25

(2) INFORMATION FOR SEQ ID NO:19:

(i) SEQUENCE CHARACTERISTICS:
           (A) LENGTH: 40 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Oligonucleotide probe for
               P. berghei 182 fragment"

(iii) HYPOTHETICAL: YES (iv) ANTI-SENSE: YES (xi) SEQUENCE DESCRIPTION: SEQ ID NO:19:

AAGGATCCAA TAATCTGATA TTGAGCAGCA TAATTGTTTC                             40

(2) INFORMATION FOR SEQ ID NO:20:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Oligonucleotide primer for
               P. berghei carboxyl cysteine rich domain"

(iii) HYPOTHETICAL: NO (iv) ANTI-SENSE: NO (xi) SEQUENCE DESCRIPTION: SEQ ID NO:20:

-continued

```
GAAGGATCCA ATTATGAAAC GCGCCATATT G                                    31
```

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            the antisence of P. berghei carboxyl cysteine rich
            domain"

(iii) HYPOTHETICAL: NO (iv) ANTI-SENSE: YES (xi) SEQUENCE DESCRIPTION: SEQ ID NO:21:

```
CTTGAATTCA AGCTTCTTGA ATATTCCTCT TTACTAAAG                             39
```

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            3' region of P. berghei carboxyl cysteine rich domain"

(iii) HYPOTHETICAL: NO (iv) ANTI-SENSE: NO (xi) SEQUENCE DESCRIPTION: SEQ ID NO:22:

```
GAAACAATTA TGCTGCAATA TCAGATTATT                                      30
```

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer for
            the antisense of the 3' untranslated region of P.
            berghei MAEBL"

(iii) HYPOTHETICAL: NO (iv) ANTI-SENSE: YES (xi) SEQUENCE DESCRIPTION: SEQ ID NO:23:

```
CATATTTTGT GTTGTATAAA C                                               21
```